(12) United States Patent
Kang et al.

(10) Patent No.: US 11,793,772 B2
(45) Date of Patent: Oct. 24, 2023

(54) PHARMACEUTICAL COMPOSITION COMPRISING THA AS ACTIVE INGREDIENT FOR TREATING BREAST CANCER

(71) Applicant: KOREA UNITED PHARM. INC., Sejong (KR)

(72) Inventors: Keon Wook Kang, Seoul (KR); Kwang-Seok Oh, Daejeon (KR); Youngchul Kim, Gwangju (KR); Sung Baek Jeong, Seoul (KR)

(73) Assignee: KOREA UNITED PHARM. INC., Sejong (KR)

( * ) Notice: Subject to any disclaimer, the term of this patent is extended or adjusted under 35 U.S.C. 154(b) by 0 days.

(21) Appl. No.: 16/343,494

(22) PCT Filed: Oct. 19, 2017

(86) PCT No.: PCT/KR2017/011595
§ 371 (c)(1),
(2) Date: Apr. 19, 2019

(87) PCT Pub. No.: WO2018/074862
PCT Pub. Date: Apr. 26, 2018

(65) Prior Publication Data
US 2019/0262281 A1 Aug. 29, 2019

(30) Foreign Application Priority Data
Oct. 21, 2016 (KR) ........................ 10-2016-0137599

(51) Int. Cl.
| | | |
|---|---|---|
| *A61K 31/12* | (2006.01) | |
| *A23L 33/105* | (2016.01) | |
| *A61P 35/00* | (2006.01) | |
| *A61K 9/00* | (2006.01) | |
| *A61K 36/9066* | (2006.01) | |

(52) U.S. Cl.
CPC ............ *A61K 31/12* (2013.01); *A23L 33/105* (2016.08); *A61K 9/0019* (2013.01); *A61K 9/0053* (2013.01); *A61K 36/9066* (2013.01); *A61P 35/00* (2018.01); *A23V 2002/00* (2013.01); *A23V 2200/308* (2013.01); *A23V 2250/21* (2013.01); *A23V 2250/2112* (2013.01)

(58) Field of Classification Search
CPC combination set(s) only.
See application file for complete search history.

(56) References Cited

U.S. PATENT DOCUMENTS

2006/0074108 A1 4/2006 Gupta

FOREIGN PATENT DOCUMENTS

| KR | 10-2014-0086355 A | 7/2014 |
|---|---|---|
| KR | 10-2014-0105988 A | 9/2014 |

OTHER PUBLICATIONS

Okuda (Cancer Chemopreventive effects of constituents of Caesalpinia ferrea and related compounds, Cancer Letters 177 (2002) 119-124).*
Arbach (Epstein-Barr Virus (EBV) Genome and Expression in Breast Cancer Tissue: Effect of EBV Infection of Breast Cancer Cells on Resistance to Paclitaxel (Taxol), Journal of Virology, Jan. 2006, p. 845-853).*
Park (KR 2014/0105988, provided in the IDS dated Jun. 24, 2020 and a machine translation).*
CAS 1-(2,4,6-trihydroxyphenyl)propan-1-one (http://www.stenutz.eu/chem/solv6%20(2).php?name=1-%282%2C4%2C6-trihydroxyphenyl%29propan-1-one).*
Cho et al., "Geranyl Derivative of Phloroacetophenone Induces Cancer Cell-Specific Apoptosis through Bax-Mediated Mitochondrial Pathway in MCF-7 Human Breast Cancer Cells", Biol. Pharm. Bull., 2012, vol. 35, No. 1, pp. 98-104.
Cho, "Apoptosis-inducing activity of synthetic polyphenol compound, 3-geranyl-2,4,6-trihydroxyacetophenone, in MCF-7 and adriamycin-resistant MCF-7 breast cancer cells", Master Thesis of Yeungnam University, 2009.
Ferreira et al., "The (2',4',6'-trihydroxyacetophenone isolated from Myrcia multiflora has antiobesity and mixed hypolipidemic effects with the reduction of lipid intestinal absorption", Planta Medica, 2011, vol. 77, No. 14, pp. 1569-1574.
Rezk et al., "The antioxidant activity of phloretin: the disclosure of a new antioxidant pharmacophore in flavonoids", Biochemical and Biophysical Research Communications, 2002, vol. 295, No. 1, pp. 9-13.
Winuthayanon et al., "Diarylheptanoid Phytoestrogens Isolated from the Medicinal Plant Curcuma comosa: Biologic Actions in Vitro and in Vivo Indicate Estrogen Receptor-Dependent Mechanisms", Environmental Health Perspectives, 2009, vol. 117, No. 7, pp. 1155-1161.

* cited by examiner

*Primary Examiner* — Kathrien A Hartsfield
(74) *Attorney, Agent, or Firm* — Vorys, Sater, Seymour and Pease LLP; Mih Suhn Koh

(57) ABSTRACT

Provided is a composition comprising 2,4,6-trihydroxyacetophenone (THA) as an active ingredient, and a method for preventing, alleviating or treating breast cancer using the composition by inhibiting the activity of polo-like kinase 1 (PlK1).

4 Claims, 22 Drawing Sheets

FIG. 11A

| Cell | IC50 (µM) | Plk1 |
|---|---|---|
| MCF-7 | 28.52 ± 3.5 | Low |
| SKBR3 | 6.44 ± 2.3 | Low |
| T47D | 39.62 ± 10.0 | Low |
| HCC1428 | 25.35 ± 11.2 | High |
| MDA-MB-453 | 20.93 ± 9.6 | Med |
| MDA-MB-231 | 41.00 ± 9.9 | Low |
| MDA-MB-468 | 27.96 ± 0.0 | Low |
| HCC38 | 20.90 ± 6.7 | Med |
| HCC70 | 31.02 ± 0.1 | Med |
| HCC1937 | 25.89 ± 16.0 | Med |
| TAMR-MCF-7 | 11.00 ± 2.1 | High |

Table 3.

- Value < 3: low
- 3 < value < 6: medium
- 6 < value < 9: high

PHARMACEUTICAL COMPOSITION COMPRISING THA AS ACTIVE INGREDIENT FOR TREATING BREAST CANCER

STATEMENT REGARDING GOVERNMENT RIGHTS

The present invention was undertaken with the support of "Pre-clinical study of trihydroxyacetophenone(THE), a polo-like kinase1 polo-box domain inhibitor, as a candidate of novel anticarcinogenic substance" No. HI18C1391 grant funded by the Korea Health Industry Development Institute.

CROSS-REFERENCE TO RELATED APPLICATIONS

This application is a 371 of PCT/KR2017/011595, filed Oct. 19, 2017, which claims the benefit of priority from Korean Patent Application No. 10-2016-0137599, filed Oct. 21, 2016, the contents of each of which are incorporated herein by reference in its entirety.

TECHNICAL FIELD

The present invention relates to a composition for preventing, alleviating, or treating breast cancer, which comprises 2,4,6-trihydroxyacetophenone (THA) as an active ingredient.

BACKGROUND ART

*Curcuma comosa* is a turmeric plant widely used as a raw material of health functional foods in Southeast Asia such as Thailand, Vietnam, and the like, and particularly, is known to be effective for vaginal atrophy, vasodilation, or the like in postmenopausal women due to its estrogen-like action, which is a female hormone. The diarylhepatanoid series is known as an active ingredient of *Curcuma comosa*, and the compound has been found to affect hepatocyte protection (liver protection), the inhibition of melanin production (whitening), or the promotion of osteoblast differentiation (improvement of osteoporosis). In addition, it is known that a *Curcuma comosa* extract has an effect of reducing blood cholesterol, which is known to be an action of 2,4,6-trihydroxyacetophenone (THA, phloracetophenone), which is another active ingredient of *Curcuma comosa*, but there has been no report of the anticancer activity of the compound.

Meanwhile, among women, in the United States, breast cancer is the most common type of cancer and in Korea, is the second most common type of cancer according to statistical data in 2008. In Korea, the incidence rate of breast cancer has increased at an annual rate of 6.8% since 2000, which is the fastest rate of increase in the world (reported by WHO in 2010). According to statistics of the Korea Health Industry Development Institute in 2012 and 2013, about 885,735 of a total of 3,232,417 medical checkup patients were diagnosed with breast cancer, and are paying high medical costs, ranking second among cancer patients in the nation. Considering the increasing incidence rate of breast cancer in Korea, it is very important to treat breast cancer, and the development of a pharmaceutical composition is required.

In particular, patients administered SERM-based anticancer agents such as tamoxifen, respond to the drug at the early stage, but approximately 50% of them are less likely to respond to the drug and have resistance to tamoxifen. Recent research results have shown that, when other signals other than tamoxifen, e.g., mTOR signaling, are inhibited, or vorinostat, which is a HDAC inhibitor, and tamoxifen were co-administered, it was effective for tamoxifen-resistant breast cancer. However, these two methods are not very effective, and have been found to cause various side effects. Since the mechanism of tamoxifen resistance has not yet been clearly found, suitable therapeutic drugs have not been developed.

Polo-like kinase 1 (Plk1), which is one of the Plk family, is a kinase protein expressed only in adult tissues being proliferated and cells being divided. The expression level of Plk1 is an indicator of cell proliferation, and thus may track the malignancy of various types of cancer. In addition, it has been reported that a high expression level of Plk1 in cancer tissues is associated with not only proliferation but also metastasis. It is reported that the mutation of P53, which is a typical cause of cancer malignancy in various cancer tissues, is associated with the expression level of Plk1, and the mutation of P53 causes the activation of Plk1, which leads to cancer malignancy.

That is, Plk1, which is a serine/threonine kinase, corresponds to a key signal of cancer cell proliferation through cell division that regulates centrosome formation, bipolar spindle formation, the chromosome skeleton, and blastomere formation. Plk1 activated during cancer cell proliferation activates cdc25c, and the activated cdc25c dephosphorylates cyclin B1, thereby inducing the mitosis of cancer cells. This results in cancer cell proliferation, and for this reason, many synthetic Plk1 inhibitors have entered clinical trials as anticancer drugs, such as Volasertib which has recently been approved as an orphan drug for the treatment of leukemia. In addition, Plk1 has recently attracted attention as a therapeutic target in various types of leukemia and solid cancers, and the applicability of Plk1 as a drug target has also been proposed for chemotherapy-resistant carcinomas such as androgen-resistant prostate cancer cells, gemcitabine-resistant pancreatic cancer cells, imatinib-resistant chronic myelogenous leukemia, docetaxel-resistant lung cancer cells, and the like. However, the potential of Plk1 for treating hormone-resistant breast cancer has never been evaluated (Korean Patent Publication No. 10-2014-0086355).

DISCLOSURE

Technical Problem

The present invention has been made to address the above-described problems of the related art, and as a result of having studied and made efforts to develop a drug for inhibiting Plk1 activity, the inventors of the present invention first verified that 2,4,6-trihydroxyacetophenone (THA), which is a main component of *Curcuma comosa*, induced the inhibition of Plk1 activity to thereby inhibit the progression of hormone-resistant breast cancer, and thus completed the present invention.

Therefore, an object of the present invention is to provide a pharmaceutical composition for preventing or treating breast cancer, which comprises a *Curcuma comosa* extract as an active ingredient.

Another object of the present invention is to provide a pharmaceutical composition for preventing or treating breast cancer, which comprises 2,4,6-trihydroxyacetophenone (THA) represented by Formula 1 below or a pharmaceutically acceptable salt thereof as an active ingredient.

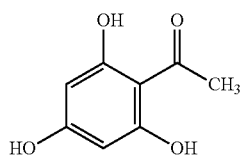

[Formula 1]

Still another object of the present invention is to provide a health functional food composition for alleviating breast cancer, which comprises a *Curcuma comosa* extract as an active ingredient.

Yet another object of the present invention is to provide a health functional food composition for alleviating breast cancer, which comprises 2,4,6-trihydroxyacetophenone (THA) represented by Formula 1 below or a pharmaceutically acceptable salt thereof as an active ingredient.

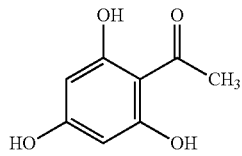

[Formula 1]

However, technical problems to be solved by the present invention are not limited to the above-described technical problems, and other unmentioned technical problems will become apparent to those of ordinary skill in the art from the following description.

Technical Solution

According to an aspect of the present invention, there is provided a pharmaceutical composition for preventing or treating breast cancer, which comprises 2,4,6-trihydroxyacetophenone (THA) represented by Formula 1 below or a pharmaceutically acceptable salt thereof as an active ingredient.

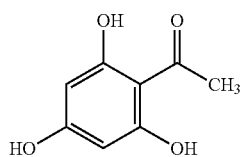

[Formula 1]

In one embodiment of the present invention, the breast cancer may be tamoxifen-resistant breast cancer or polo-like kinase 1 (Plk1)-overexpressing breast cancer, but the present invention is not limited thereto.

In another embodiment of the present invention, the composition may inhibit the activity of polo-like kinase 1 (Plk1).

The present invention also provides a health functional food composition for alleviating breast cancer, which comprises 2,4,6-trihydroxyacetophenone (THA) represented by Formula 1 below or a pharmaceutically acceptable salt thereof as an active ingredient.

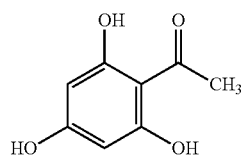

[Formula 1]

In one embodiment of the present invention, the breast cancer may be tamoxifen-resistant breast cancer or polo-like kinase 1 (Plk1)-overexpressing breast cancer, but the present invention is not limited thereto.

In another embodiment of the present invention, the composition may inhibit the activity of polo-like kinase 1 (Plk1).

The present invention also provides a method of treating breast cancer, which comprises administering a pharmaceutical composition comprising 2,4,6-trihydroxyacetophenone (THA) as an active ingredient to an individual in need of treatment of breast cancer.

The present invention also provides a use of a pharmaceutical composition comprising 2,4,6-trihydroxyacetophenone (THA) as an active ingredient for treating breast cancer.

Advantageous Effects

The present invention relates to a composition for preventing, alleviating, or treating breast cancer, which comprises 2,4,6-trihydroxyacetophenone (THA) as an active ingredient. More particularly, the THA of the present invention is extracted from *Curcuma comosa*, and when a tamoxifen-resistant breast cancer cell line is treated with THA, the THA inhibits the activity of polo-like kinase 1 (Plk1), thereby having an excellent effect of inhibiting the proliferation of breast cancer cells, and thus it is anticipated that THA can be effectively used for preventing, alleviating, and treating tamoxifen-resistant breast cancer or polo-like kinase 1 (Plk1)-overexpressing breast cancer.

DESCRIPTION OF DRAWINGS

FIGS. 11A and 11B illustrate results of confirming changes in THA reactivity according to Plk1 expression differences per human breast cancer cell line.

MODES OF THE INVENTION

Figure 1:
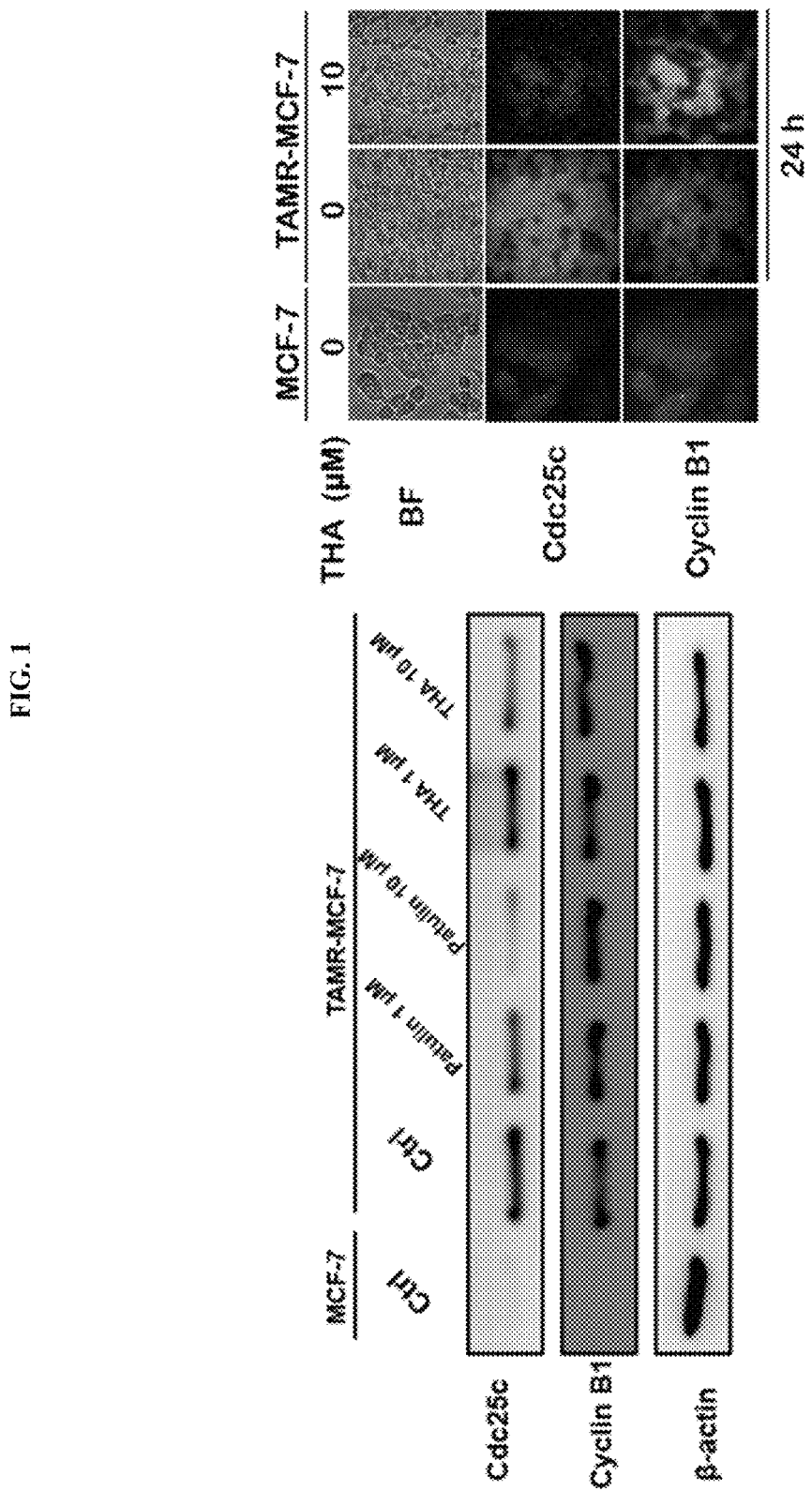
FIG. 1 illustrates western blotting and immunocytochemistry results of confirming a decrease in the expression of cdc25C, which is a downstream signal of Plk1, and a compensatory increase in cyclin B1 in tamoxifen-resistant breast cancer cells upon treatment with 2,4,6-trihydroxyacetophenone (THA).

The inventors of the present invention have verified that a *Curcuma comosa* extract and its active ingredient, i.e., 2,4,6-trihydroxyacetophenone (THA) compound, are effective anticancer agents for inhibiting the proliferation of breast cancer, particularly hormone-resistant breast cancer, and confirmed that this action is due to Plk1 inhibition, thus completing the present invention on these findings.

Hereinafter, the present invention will be described in detail.

In one embodiment of the present invention, as a result of examining whether the inhibition of Plk1 activity induces the inhibition of cell proliferation, upon treatment with THA, the expression of cdc25c, which is a downstream signal of Plk1, decreased and cyclin B1 expression increased, from which it was confirmed that Plk1 activity was inhibited and selective proliferation of hormone-resistant breast cancer was inhibited (see Example 2).

In another embodiment of the present invention, as a result of examining whether tumor proliferation was inhibited in a tamoxifen-resistant breast cancer xenograft mouse model when intraperitoneally administered THA, it was confirmed that, in a group into which THA was intraperitoneally injected at a dose of 6 mg/kg, tumor proliferation was inhibited, PCNA, which is a cell proliferation marker, was significantly decreased, and TUNEL, which is an apoptosis marker, was significantly increased. In addition, it was observed that excellent anticancer activity was exhibited in a tamoxifen-resistant breast cancer cell xenograft mouse model upon oral administration of THA at a dose of 10 mg/kg, 30 mg/kg, or 100 mg/kg, from which it was confirmed that THA was an effective oral drug (see Example 3).

In another embodiment of the present invention, Plk1 expression patterns in tissues and cells of human breast cancer patients were confirmed (see Example 4), and the THA reactivity of each human breast cancer cell line was confirmed (see Example 5).

Therefore, 2,4,6-trihydroxyacetophenone (THA) according to the present invention may be used for various purposes and applications requiring the prevention or treatment of breast cancer or hormone-resistant breast cancer.

Therefore, the present invention provides a related product and/or related method comprising a composition for alleviating, preventing, or treating breast cancer or hormone-resistant breast cancer, which comprises, as an active ingredient, a *Curcuma comosa* extract, 2,4,6-trihydroxyacetophenone (THA) represented by Formula 1 below, or a pharmaceutically acceptable salt thereof.

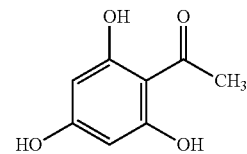

[Formula 1]

The present invention provides a pharmaceutical composition for preventing or treating breast cancer or hormone-resistant breast cancer, which comprises, as an active ingredient, a *Curcuma comosa* extract, 2,4,6-trihydroxyacetophenone (THA) represented by Formula 1 below, or a pharmaceutically acceptable salt thereof.

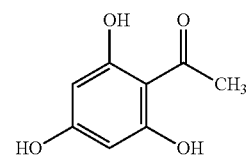

[Formula 1]

The term "prevention" as used herein means all actions that inhibit breast cancer or hormone-resistant breast cancer or delay the onset thereof via administration of the composition of the present invention.

The term "treatment" as used herein means all actions that alleviate or beneficially change symptoms due to breast cancer or hormone-resistant breast cancer via administration of the composition of the present invention.

The term "pharmaceutically acceptable" as used herein refers to a compound or composition that is suitable for use in contact with the tissue of a subject (e.g., humans) since a benefit/risk ratio is reasonable without excessive toxicity, irritation, allergic responses, or other problems or complications, and is within the scope of sound medical determination.

The term "salt" as used herein refers to an acid addition salt formed by a pharmaceutically acceptable free acid. The acid addition salt is obtained from: inorganic acids such as hydrochloric acid, nitric acid, phosphoric acid, sulfuric acid, hydrobromic acid, hydriodic acid, nitrous acid, and phosphorous acid; or nontoxic organic acids such as aliphatic mono- and dicarboxylates, phenyl-substituted alkanoates, hydroxy alkanoates and alkandioates, aromatic acids, and aliphatic and aromatic sulfonic acids. Examples of these pharmaceutically nontoxic salts include sulfates, pyrosulfates, bisulfates, sulfites, bisulfites, nitrates, phosphates, monohydrogen phosphates, dihydrogen phosphates, methaphosphates, pyrophosphate chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butyne-1,4-dioates, hexane-1,6-dioates, benzoates, chlorobenzoates, methylbenzoates, dinitro benzoates, hydroxybenzoates, methoxybenzoates, phthalates, terephthalates, benzenesulfonates, toluenesulfonates, chlorobenzene sulfonates, xylenesulfonates, phenylacetates, phenylpropionates, phenylbutyrates, citrates, lactates, β-hydroxybutyrates, glycolates, maleates, tartrates, methanesulfonates, propanesulfonates, naphthalene-1-sulfonates, naphthalene-2-sulfonates, and mandelates.

Acid addition salts according to the present invention may be prepared using a conventional method, for example, by dissolving the compound of Formula 1 in an excess of an aqueous acid solution and precipitating the salt using a water-miscible organic solvent, e.g., methanol, ethanol, acetone, or acetonitrile. The acid addition salts may also be prepared by evaporating and drying the solvent or an excess of acid in the mixture or suction-filtering the precipitated salt.

In addition, pharmaceutically acceptable metallic salts may be prepared using bases. Alkali metal or alkaline earth metal salts are obtained by, for example, dissolving a compound in an excess of an alkali metal hydroxide or alkaline earth metal hydroxide solution, filtering a non-soluble compound salt, and evaporating and drying the filtrate. At this time, it is pharmaceutically preferable that a sodium salt, a potassium salt, or a calcium salt is prepared as a metal salt. Silver salts corresponding thereto are obtained by reacting an alkali metal or an alkaline earth metal salt with a suitable silver salt (e.g., silver nitrate).

The pharmaceutical composition of the present invention includes a pharmaceutically acceptable carrier, in addition to the active ingredient. The pharmaceutically acceptable carrier, which is commonly used in formulation, may include lactose, dextrose, sucrose, sorbitol, mannitol, starch, acacia gum, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but the present invention is not limited to the above examples. The pharmaceutical composition may further include, in addition to the above-described components, a lubricant, a wetting agent, a sweetener, a flavor enhancer, an emulsifying agent, a suspension agent, a preservative, or the like.

The pharmaceutical composition of the present invention may be administered orally or parenterally (e.g., intravenous administration, subcutaneous administration, intraperitoneal administration, or topical administration) according to a target method, and a suitable dose thereof may vary depending on the condition and body weight of a patient, the severity of disease, the type of drug, administration routes, and administration time, and may be appropriately selected by those of ordinary skill in the art.

The pharmaceutical composition of the present invention is administered in a pharmaceutically effective amount. The term "pharmaceutically effective amount" as used herein refers to an amount sufficient to treat diseases at a reasonable benefit/risk ratio applicable to medical treatment, and an effective dosage level may be determined according to factors including the type of disease of a patient, the severity of disease, drug activity, sensitivity to a drug, administration time, administration routes, excretion rate, treatment period, and simultaneously used drugs, and other factors well known in the medical field. The pharmaceutical composition according to the present invention may be administered as an individual therapeutic agent or in combination with other therapeutic agents, may be administered consecutively or simultaneously with existing therapeutic agents, and may be administered in a single dose or multiple doses. It is important to administer the composition in the minimum amount that enables achievement of the maximum effects without side effects in consideration of all the above-described factors, and this may be easily determined by those of ordinary skill in the art.

In particular, an effective amount of the pharmaceutical composition according to the present invention may vary according to the age, gender, condition, and body weight of a patient, the absorption of the active ingredient in the body, inactivation rate and excretion rate, the type of a disease, and simultaneously used drugs. Generally, the pharmaceutical composition may be administered in an amount of 0.001 mg to 150 mg, preferably, 0.01 mg to 100 mg, per body weight (1 kg) daily or every other day, or may be administered once or three times a day. However, the dosage may be increased or decreased according to administration routes, the severity of disease, gender, body weight, age, and the like, and thus the dosage is not intended to limit the scope of the present invention in any way.

The term "cancer," which is a disease to be prevented or treated by the composition of the present invention, refers to a disease in which normal tissue cells grow unlimitedly for some reason and continue to develop rapidly regardless of the life phenomenon of the living body, the surrounding tissue state, or the like, and the cancer of the present invention may be breast cancer, preferably hormone-resistant breast cancer. The term "hormone-resistant" as used herein refers to the occurrence of the proliferation of breast cancer cells regardless of the presence or absence of a sex hormone.

The compound of the present invention is effective for preventing, alleviating, or treating cancer by inhibiting the proliferation of cancer cells through Plk1 inhibitory activity.

In the present invention, the THA may be extracted from *Curcuma comosa* using any method of obtaining an extract from a natural substance known in the art. Preferably, the THA may be obtained through a soluble extraction method by adding water or an organic solvent.

A process of performing extraction by adding water or an organic solvent to *Curcuma comosa* may be performed using a method, such as by stirring, standing, or the like, and extraction may be performed by a hot water extraction method, a cold extraction method, a reflux cooling extraction method, an ultrasonic extraction method, or the like once or several times. The organic solvent that may be added in this process may be, but is not limited to, methanol, ethanol, propanol, isopropanol, butanol, acetone, ether, benzene, chloroform, ethyl acetate, methylene chloride, or the like.

The present invention provides a health functional food composition for alleviating breast cancer or hormone-resistant breast cancer, which comprises, as an active ingredient, a *Curcuma comosa* extract, 2,4,6-trihydroxyacetophenone (THA) represented by Formula 1 below, or a pharmaceutically acceptable salt thereof.

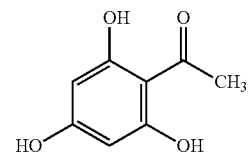

[Formula 1]

The health functional food composition according to the present invention may be used simultaneously with or separately from a medicine for the treatment of breast cancer or hormone-resistant breast cancer, in order to alleviate breast cancer or hormone-resistant breast cancer.

Similarly, the term "cancer," which is a disease to be alleviated by the composition of the present invention, refers to a disease in which normal tissue cells grow unlimitedly for some reason and continue to develop rapidly regardless of the life phenomenon of the living body, the surrounding tissue state, or the like, and the cancer of the present invention may be breast cancer, preferably hormone-resistant breast cancer. The term "hormone-resistant" as used herein refers to the occurrence of the proliferation of breast cancer cells regardless of the presence or absence of a sex hormone.

The term "alleviation" as used herein means all actions that decrease at least the degree of parameters related to conditions being treated, e.g., symptoms.

The health functional food composition according to the present invention may be added to health supplements such as foods, beverages, and the like for the purpose of alleviating breast cancer or hormone-resistant breast cancer.

The type of foods is not particularly limited, and examples of foods that may include the active ingredient include drinks, meats, sausages, bread, biscuits, rice cakes, chocolates, candies, snacks, confectionaries, pizzas, instant noodles, other noodles, gum, dairy products including ice creams, various kinds of soup, beverages, alcoholic drinks, vitamin complexes, dairy products, processed dairy products, and the like, and all health functional foods in the ordinary sense are included.

In the health functional food composition according to the present invention, the active ingredient may be added to a food directly or in combination with other foods or food ingredients, and may be appropriately used according to a general method. The amount of the active ingredient to be mixed may be appropriately determined according to the purpose of use. Generally, when preparing a food or a beverage, the composition of the present invention is added in an amount of 15 wt % or less, preferably 10 wt % or less, with respect to a total weight of raw materials of the composition. However, in the case of long-term ingestion for health and hygienic purposes or for health control purposes, the amount may be the above range or less.

A health beverage composition of the present invention may include the active ingredient as an essential ingredient at the indicated ratio, and other ingredients thereof are not particularly limited, and the health beverage composition may include additional ingredients such as various flavoring agents, natural carbohydrates, or the like as in general beverages. Examples of the above-described natural carbohydrates include general sugars such as monosaccharides, e.g., glucose, fructose, and the like; disaccharides, e.g., maltose, sucrose, and the like; and polysaccharides such as dextrin, cyclodextrin, and the like, and sugar alcohols such as xylitol, sorbitol, erythritol, and the like. As a flavoring agent other than the above-described flavoring agents, a natural flavoring agent (thaumatin and stevia extracts (e.g., rebaudioside A, glycyrrhizin, and the like) and a synthetic flavoring agent (saccharin, aspartame, and the like) are preferably used. The proportion of the natural carbohydrates may be appropriately determined by selection of those of ordinary skill in the art.

In addition to the above-listed ingredients, the health functional food composition of the present invention may include various nutritional supplements, vitamins, minerals (electrolytes), flavors such as synthetic flavors, natural flavors, and the like, colorants and enhancers (cheese, chocolates, and the like), pectic acid and salts thereof, alginic acid and salts thereof, organic acids, a protective colloid thickener, a pH adjuster, a stabilizer, a preservative, glycerin, alcohols, a carbonating agent used in carbonated beverages, and the like. These ingredients may be used alone or a combination thereof may be used. The proportion of these additives may also be appropriately selected by those of ordinary skill in the art.

The present invention also provides a method of treating breast cancer or hormone-resistant breast cancer, which comprises administering the pharmaceutical composition to an individual. The term "individual" as used herein refers to a subject with a disease requiring treatment and, more particularly, includes mammals such as humans, non-human primates, mice, dogs, cats, horses, cows, and the like.

Hereinafter, examples of the present invention will be described to aid in understanding of the present invention. However, these examples are provided only to facilitate the understanding of the present invention and are not intended to limit the scope of the present invention.

EXAMPLES

Example 1. Experimental Preparation and Experimental Methods 1-1. Reagents and Materials A cdc25c antibody was purchased from Cell Signaling Technology (Beverly, Mass., USA) and a cyclin B1 antibody and 2,4,6-trihydroxyacetophenone (THA) were purchased from Santa Cruz Biotechnology (Dallas, Tex. USA). A β-actin antibody was purchased from Sigma (St. Louis, Mo., USA), and *Curcuma comosa* was supplied from Korea United Pharmaceutical Co., Ltd.

1-2. Cell Line Culture

An MCF-7 cell line was sub-cultured in high glucose Dulbeccos Modified Eagle's Medium (DMEM) containing 10% fetal bovine serum, 50 U/ml of penicillin, and 50 μg/ml of streptomycin in an incubator supplied with 5% $CO_2$ at 37° C. to be used for experiments. A TAMR-MCF-7 cell line was cultured in high glucose Dulbeccos Modified Eagle's Medium (DMEM) containing 10% charcoal-stripped fetal bovine serum, 3 μM 4-OH-tamoxifen (Sigma-Aldrich, Mo., USA), 50 U/ml of penicillin, and 50 μg/ml of streptomycin.

1-3. Immunochemical Analysis

Sodium dodecyl sulfate-polyacrylamide gel electrophoresis (SDS-PAGE) was performed using a gel electrophoresis apparatus (Mighty Small SE250, Hoefer Scientific Instruments, San Francisco). A cell lysate fraction was diluted in a sample dilution buffer [63 mM Tris (pH 6.8), 10% glycerol, 2% SDS, 0.0013% bromophenol blue, and 5% β-mercaptoethanol], and then electrophoresis was performed thereon in an electrode buffer (15 g of Tris, 72 g of glycerin, and 5 g of SDS included in a 1 L solution) using a 8% to 12% gel. The electrophoresed gel was used to transfer proteins to a nitrocellulose membrane at 190 mAmps for 70 minutes in a transfer buffer (25 mM Tris, 192 mM glycerin, and 20% v/v methanol (pH 8.3)) using a transfer electrophoresis apparatus. The nitrocellulose membrane was reacted with a primary antibody, and then reacted with horseradish peroxidase-conjugated goat anti-rabbit IgG and horseradish peroxidase-conjugated goat anti-mouse IgG as secondary antibodies for 6 hours, followed by color development using an ECL detection system (ECL chemiluminescence system, Amersham, Gaithersberg, Mass.).

1-4. Real-Time Cell Proliferation Assay

To measure cell proliferation, cells were plated in a 96-well dish ($5 \times 10^3$ cells/well). After drug treatment, the number of live cells was measured using an IncuCyte ZOOM live cell analysis system (Essen Bioscience, Ann Arbor, Mich., USA) at intervals of 4 hours.

1-5. Experimental Animals

In all experiments, 6-week-old female BALB/c-nu mice were raised for 1 week at the Research Center for Animal Experiments in the College of Pharmacy of the Seoul National University at a humidity of 55±5% and a temperature of 22±2° C. and under controlled ventilation conditions and adapted to the environment, and then used in the experiments according to randomized block design, and light/dark cycles were adjusted to 12 hours.

Animal experiments were carried out in accordance with the Experimental Animals Ethics Guidelines. TAMR-MCF-7 cells ($5\times10^6$ cells) were transdermally injected into the left mammary gland of nude mice, and tumor sizes were measured using a caliper twice a week. Tumor volume was calculated by the following formula: Tumor volume=length×width$^2$. Five weeks after cell transplantation, the mice were euthanized using carbon dioxide gas and the tumors were extracted and weighed.

1-6. Immunofluorescence

To measure fluorescence expression, cells were plated in a 6-well dish ($5\times10^5$ cells/well). Fluorescence was conjugated to cdc25c and cyclin B1 antibodies using SiteClick™ Qdot antibody labeling kits (Thermo Scientific, IL, USA), and fluorescence-conjugated cdc25c and cyclin B1 antibodies were treated in a 6-well dish, and then expression was observed through a fluorescence microscope.

1-7. Cell Cycle Analysis

To measure the cell cycle distribution, cells were plated in a 100 mm dish ($5\times10^5$ cells/well). The cells were fixed with PBS at 4° C., refrigerated in 70% EtOH at 4° C., and cultured for 24 hours. After removing the 70% EtOH, the cells were stained with propidium iodide (PI)/Triton X-100/DNAse-free RNAse A at 37° C. for 15 minutes. 20,000 cells per experimental group were analyzed using an FACS-Calibur™ (BD Biosciences, CA, USA) machine.

1-8. Real-Time Apoptosis Analysis

To measure apoptosis, cells were plated in a 96-well dish ($5\times10^3$ cells/well). The cells were pre-treated with the IncuCyte ZOOM™ 96-well Caspase-3/7 apoptosis assay reagent for 3 hours and treated with a drug, and then the degree of fluorescence expression was measured using an IncuCyte ZOOM™ live cell analysis system (Essen Bioscience, Ann Arbor, Mich., USA) at intervals of 4 hours.

Example 2. Confirmation of Inhibition of Plk1 Activity and Cell Proliferation by Treatment with 2,4,6-Trihydroxyacetophenone (THA) in Hormone-Resistant Breast Cancer Cells Tamoxifen-resistant breast cancer cells (TAMR-MCF-7) and/or control breast cancer cells (MCF-7) were treated with 2,4,6-trihydroxyacetophenone (THA), and then it was confirmed whether Plk1 activity and cell proliferation were inhibited, using the method of Example 1.

2-1. Confirmation of Inhibition of Polo-Like Kinase 1 (Plk1) Activity

As a result of treating tamoxifen-resistant breast cancer cells with THA, and then confirming the results using western blotting and immunocytochemistry, as illustrated in FIG. 1, THA reduced the expression of cdc25c, which is a downstream signal of Plk1 and increased compensatory cyclin B1 expression, from which it was confirmed that THA had a Plk1 inhibitory effect.

2-2. Confirmation of Inhibition of Cell Proliferation

Figure 2:
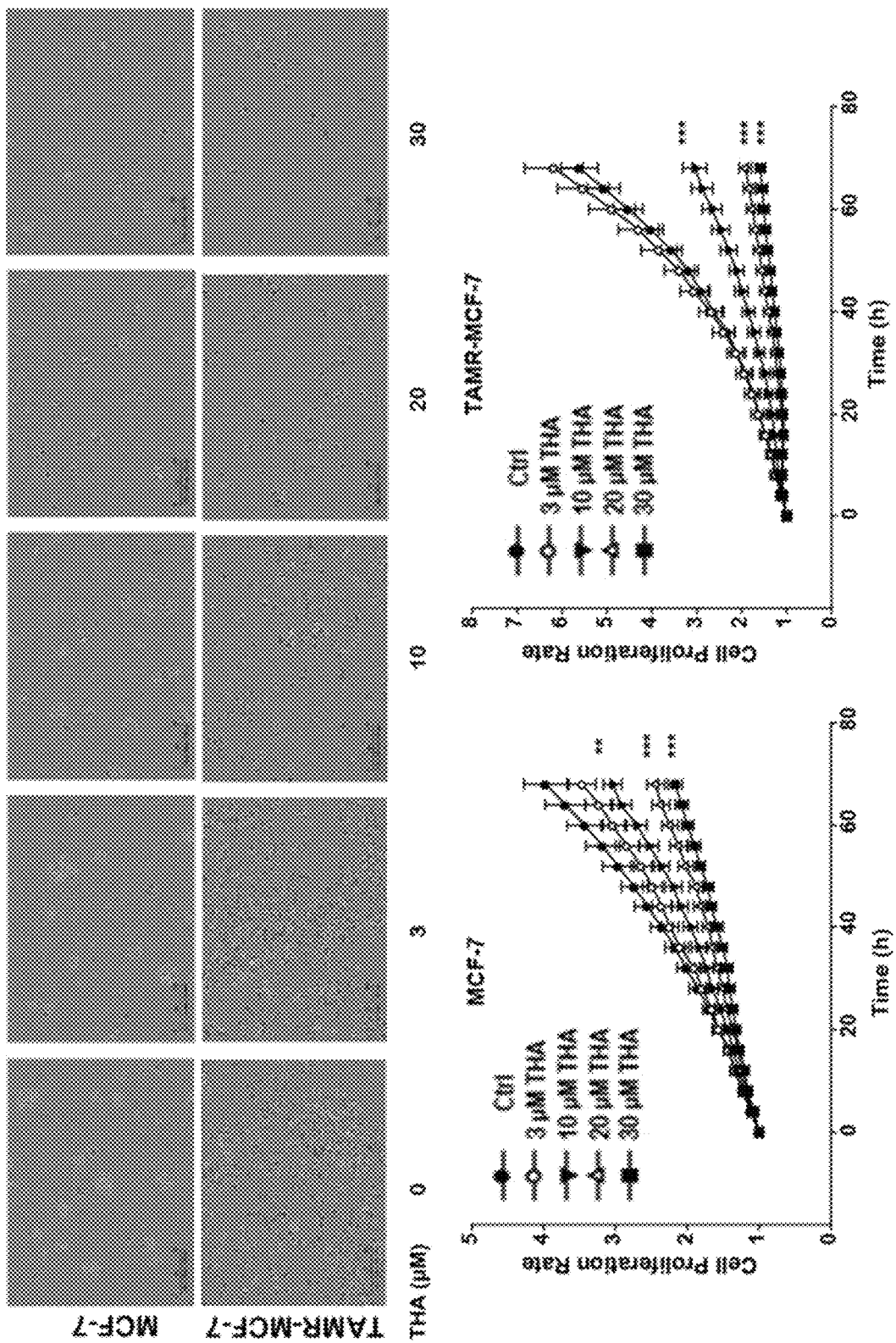
FIG. 2 illustrates results of confirming the inhibition of cell proliferation due to Plk1 activity inhibition in tamoxifen-resistant breast cancer cells (TAMR-MCF-7) and control breast cancer cells (MCF-7) after being treated with THA.

As a result of treating tamoxifen-resistant breast cancer cells and normal breast cancer cells with THA, and then performing comparative observation on whether cell proliferation was inhibited, it was confirmed as illustrated in FIG. 2 that THA inhibited cell proliferation both in MCF-7 cells, which are normal breast cancer cells, and TAMR-MCF-7 cells, which are tamoxifen-resistant breast cancer cells, and particularly, more strongly inhibited cell proliferation in the tamoxifen-resistant breast cancer cells.

Figure 3:
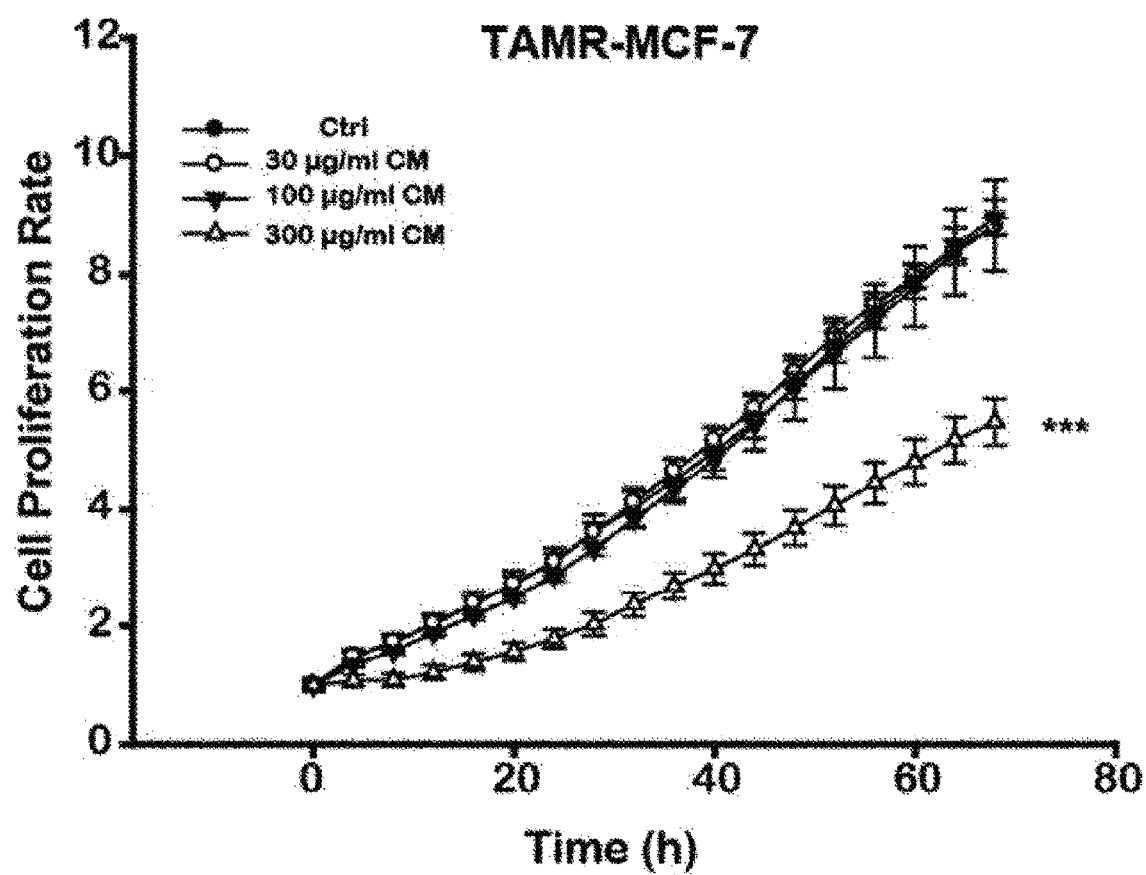
FIG. 3 is a graph showing results of confirming the inhibition of cell proliferation in tamoxifen-resistant breast cancer cells (TAMR-MCF-7) after being treated with a *Curcuma comosa* suspension.

Furthermore, as a result of treating tamoxifen-resistant breast cancer cells with a *Curcuma comosa* extract, and then observing whether cell proliferation was inhibited in the tamoxifen-resistant breast cancer cells, it was confirmed as illustrated in FIG. 3 that *Curcuma comosa* also inhibited cell proliferation in the tamoxifen-resistant breast cancer cells.

2-3. Confirmation of Cell Cycle Inhibition

Figure 4:
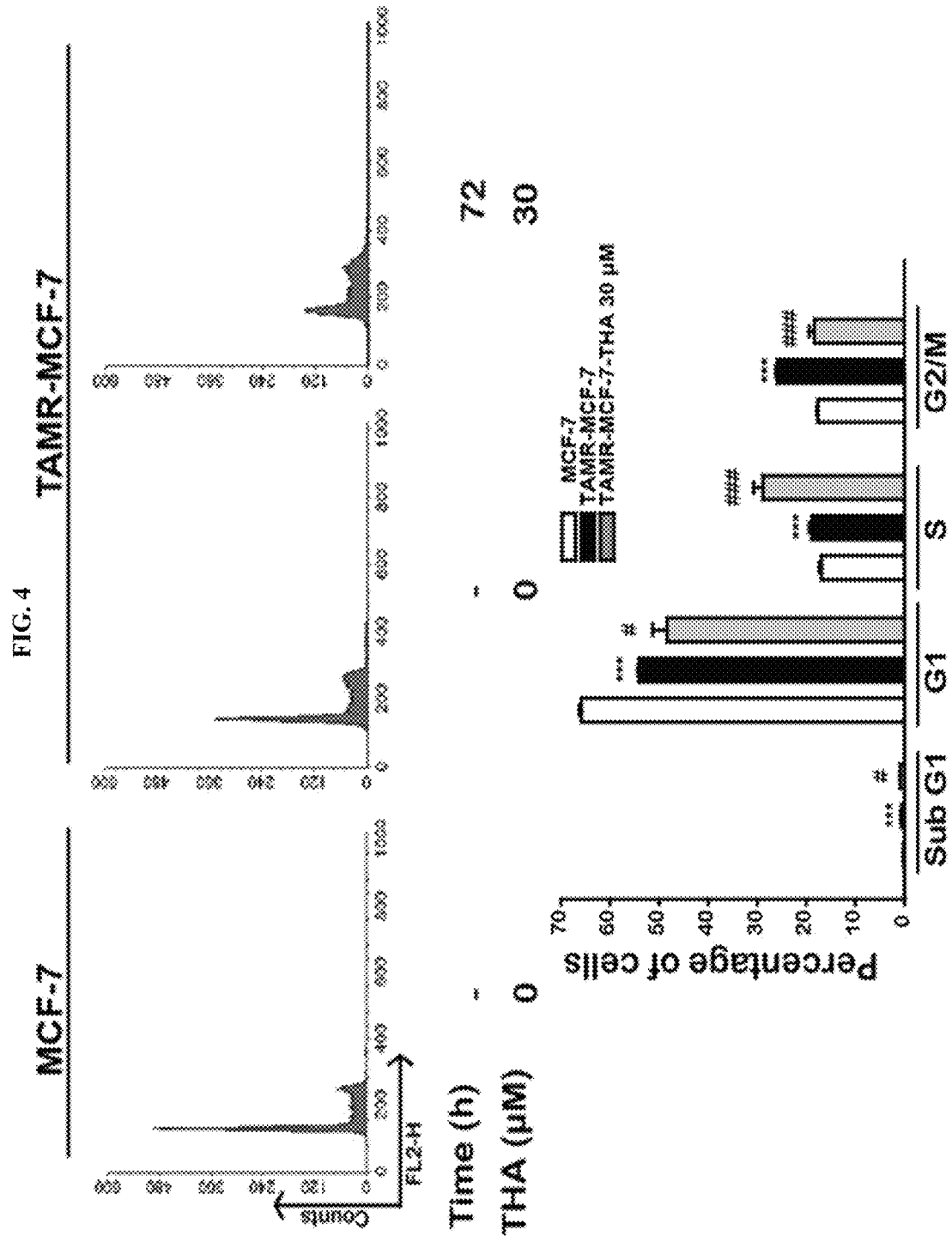
FIG. 4 illustrates results of confirming cell cycle arrest through flow cytometry after tamoxifen-resistant breast cancer cells (TAMR-MCF-7) were treated with THA.

As a result of treating tamoxifen-resistant breast cancer cells with THA, and then examining whether a cell cycle was inhibited through flow cytometry, it was confirmed as illustrated in FIG. 4 that S phase arrest, which significantly increases the number of S phase cells, occurred upon treatment with THA.

Figure 5:
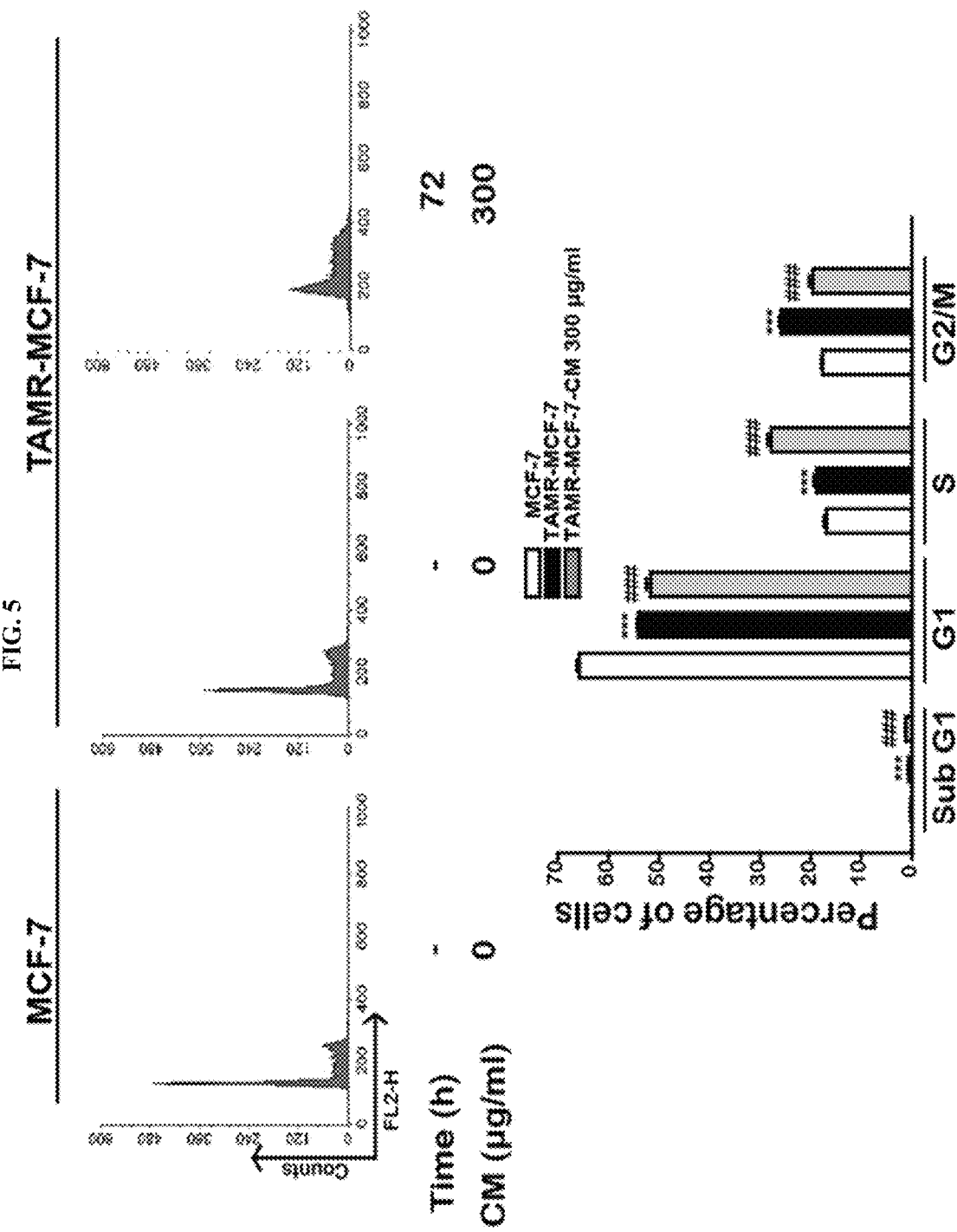
FIG. 5 illustrates results of confirming cell cycle arrest through flow cytometry after tamoxifen-resistant breast cancer cells (TAMR-MCF-7) were treated with a *Curcuma comosa* suspension.

Furthermore, as a result of treating tamoxifen-resistant breast cancer cells with a *Curcuma comosa* extract using the above-described method, and then examining whether a cell cycle was inhibited, it was confirmed as described in FIG. 5 that *Curcuma comosa* also caused S phase arrest, which significantly increases the number of S phase cells.

2-4. Confirmation of Increase in Apoptosis

Figure 6:
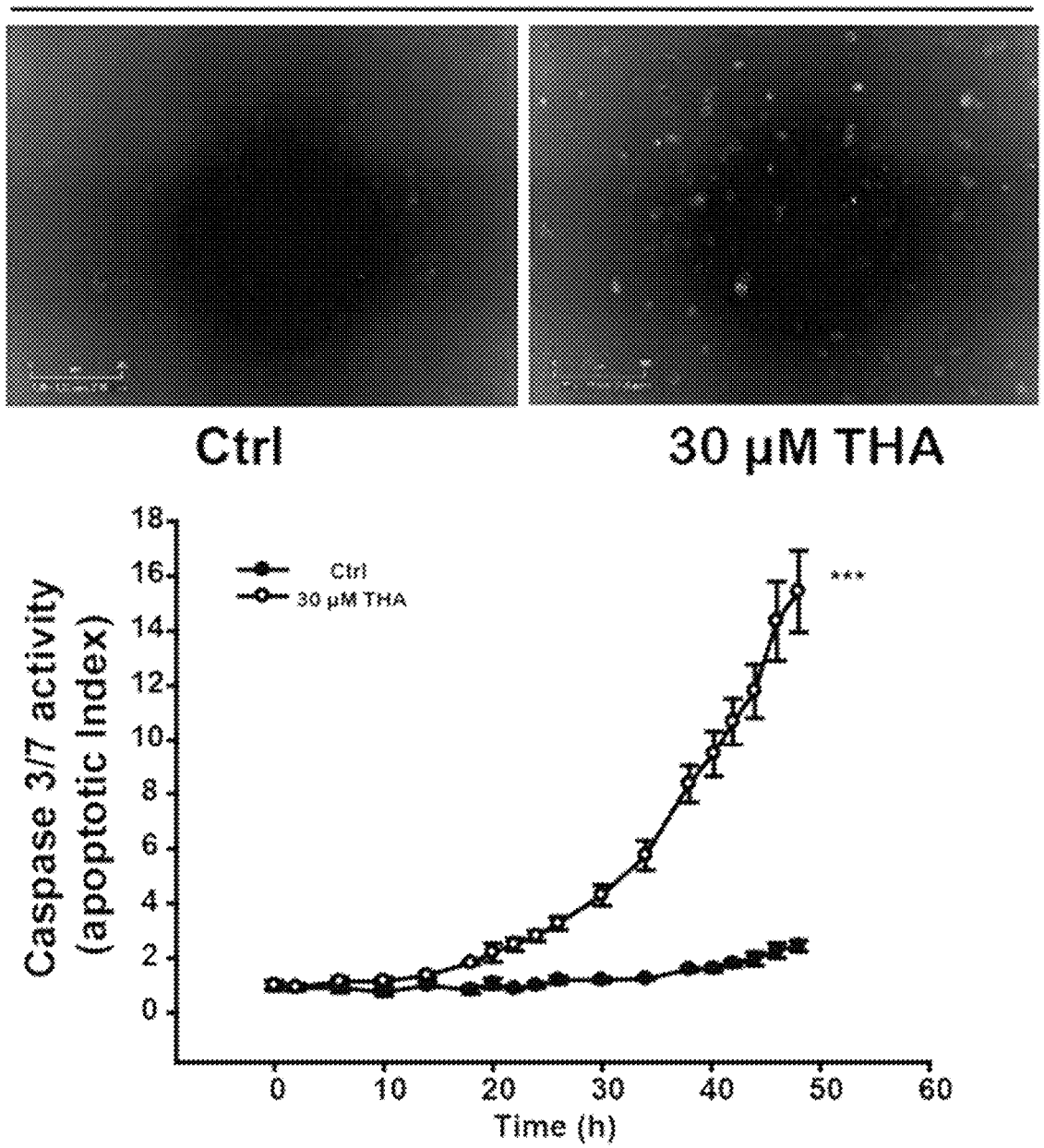
FIG. 6 illustrates results of confirming apoptosis using a caspase-3/7 fluorescent substrate after tamoxifen-resistant breast cancer cells (TAMF-MCF-7) were treated with THA.

As a result of treating tamoxifen-resistant breast cancer cells with THA, and then examining apoptosis using quantification of a capase-3/7 selective fluorescent substrate, it was confirmed as illustrated in FIG. 6 that THA significantly increased an apoptotic index.

Example 3. Confirmation of Inhibition of Plk1 Activity and Tumor Proliferation by Treatment with 2,4,6-trihydroxyacetophenone (THA) in Hormone-Resistant Breast Cancer Cell-Transplanted Nude Mice To confirm whether tumor proliferation was inhibited by treatment with 2,4,6-trihydroxyacetophenone (THA) in hormone-resistant breast cancer cell-transplanted nude mice, an experiment was carried out as follows.

THA was intraperitoneally administered to a tamoxifen-resistant breast cancer cell-transplanted mouse model every day for 2 weeks at a dose of 6 mg/kg based on a dose known to be effective for bile secretion in the liver. Tumor sizes and weights were measured twice a week during the administration period, and after administration was completed, tumors were extracted, and then the extracted tumor tissues were weighed. PCNA, which is a cell proliferative index, and TUNEL, which is an apoptotic index, were evaluated in the tumor tissues by immunohistochemistry staining, and some tissues were pulverized to quantify cdc25c, which is a downstream signal of Plk1, as a Plk1 activity index, and an increase or decrease in cdc25c expression was confirmed by western blotting.

Figure 7A:
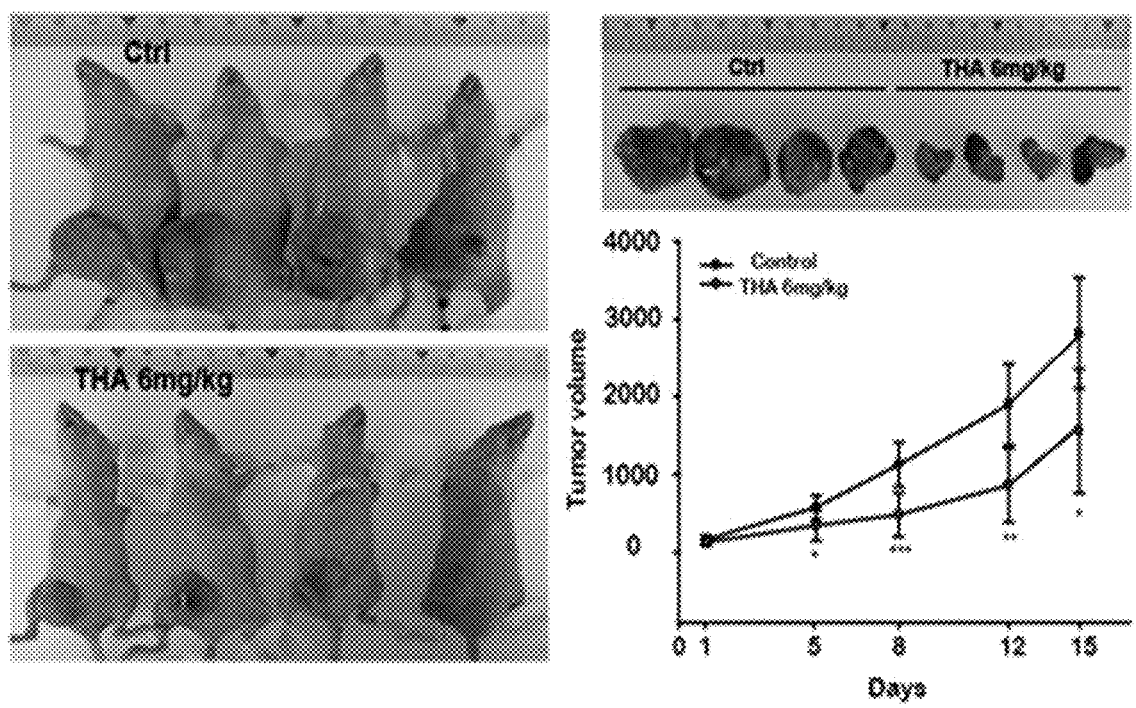
FIGS. 7A to 7F illustrate results of confirming the inhibition of tumor growth when THA was intraperitoneally administered to a xenograft mouse model transplanted with tamoxifen-resistant breast cancer cells (TAMR-MCF-7)
Figure 7B:
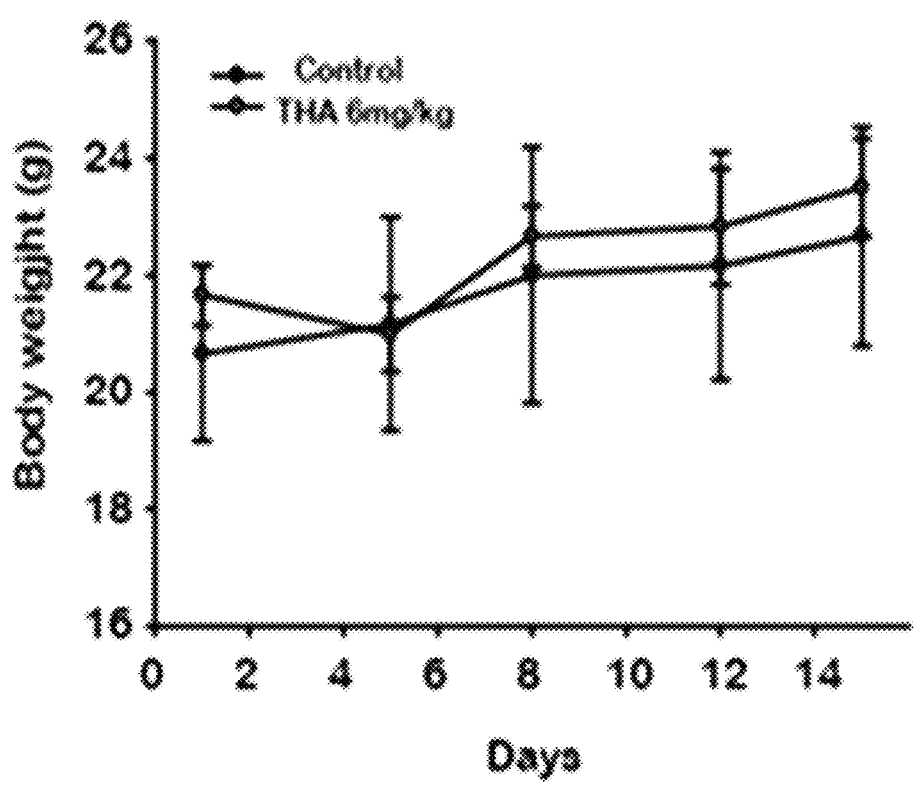
Figure 7C:
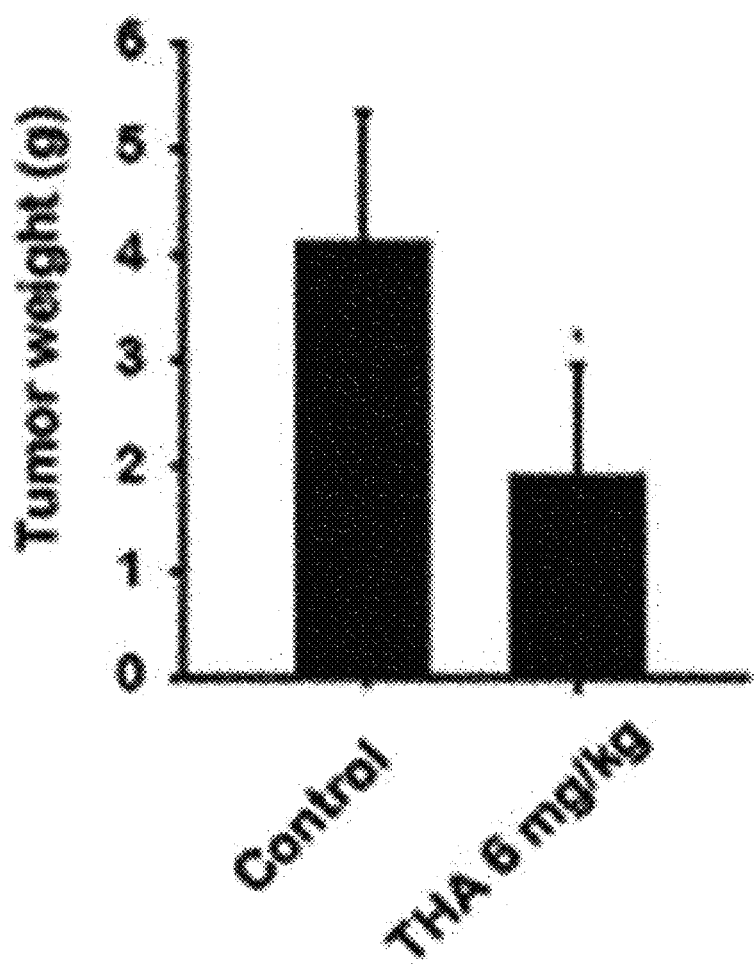
Figure 7D:
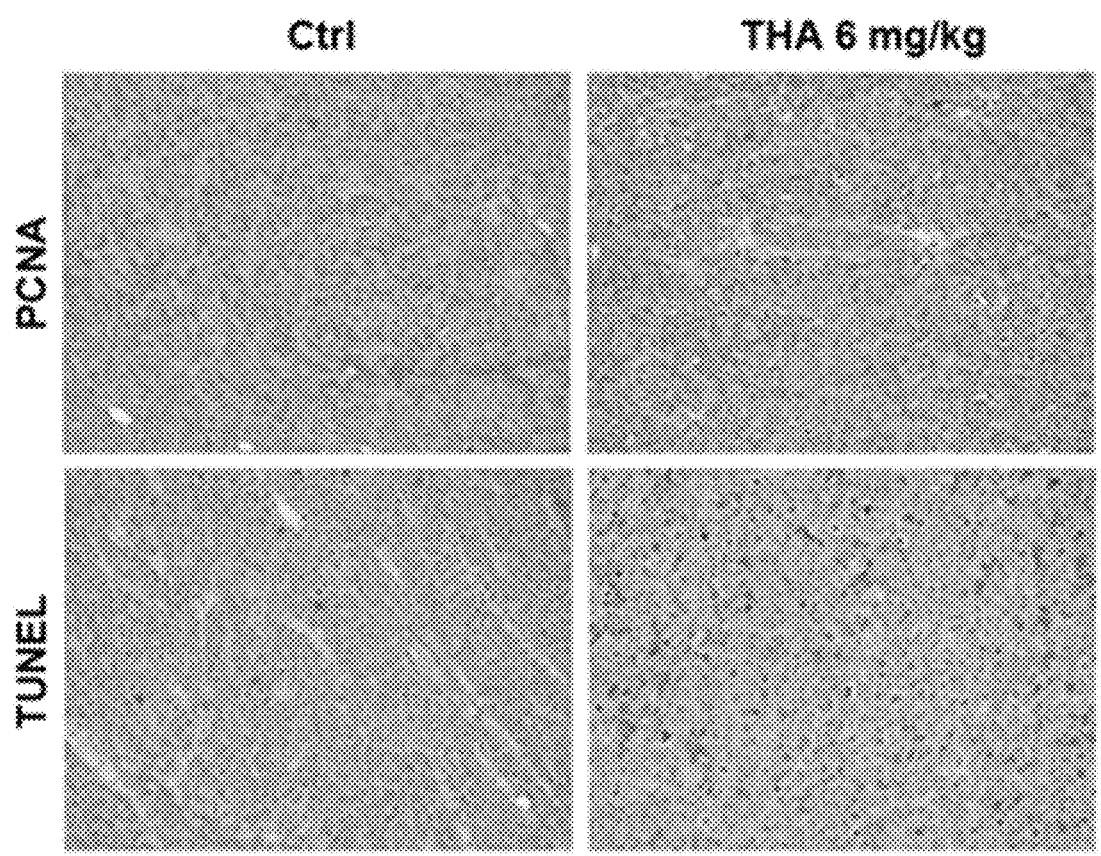
Figure 7E:
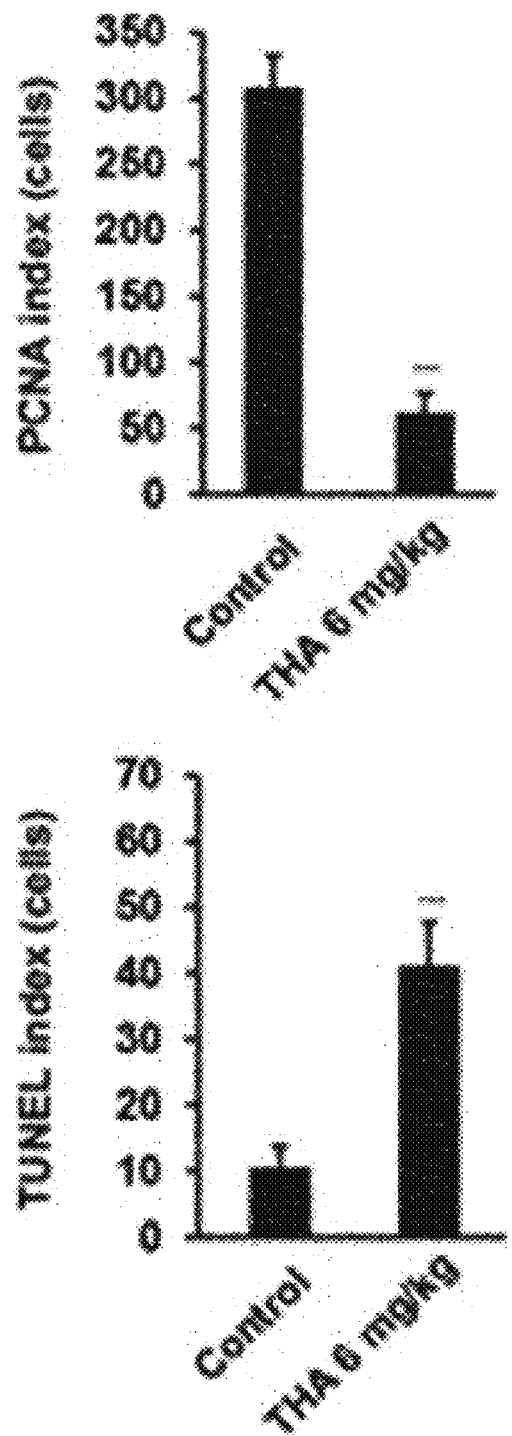
Figure 7F:
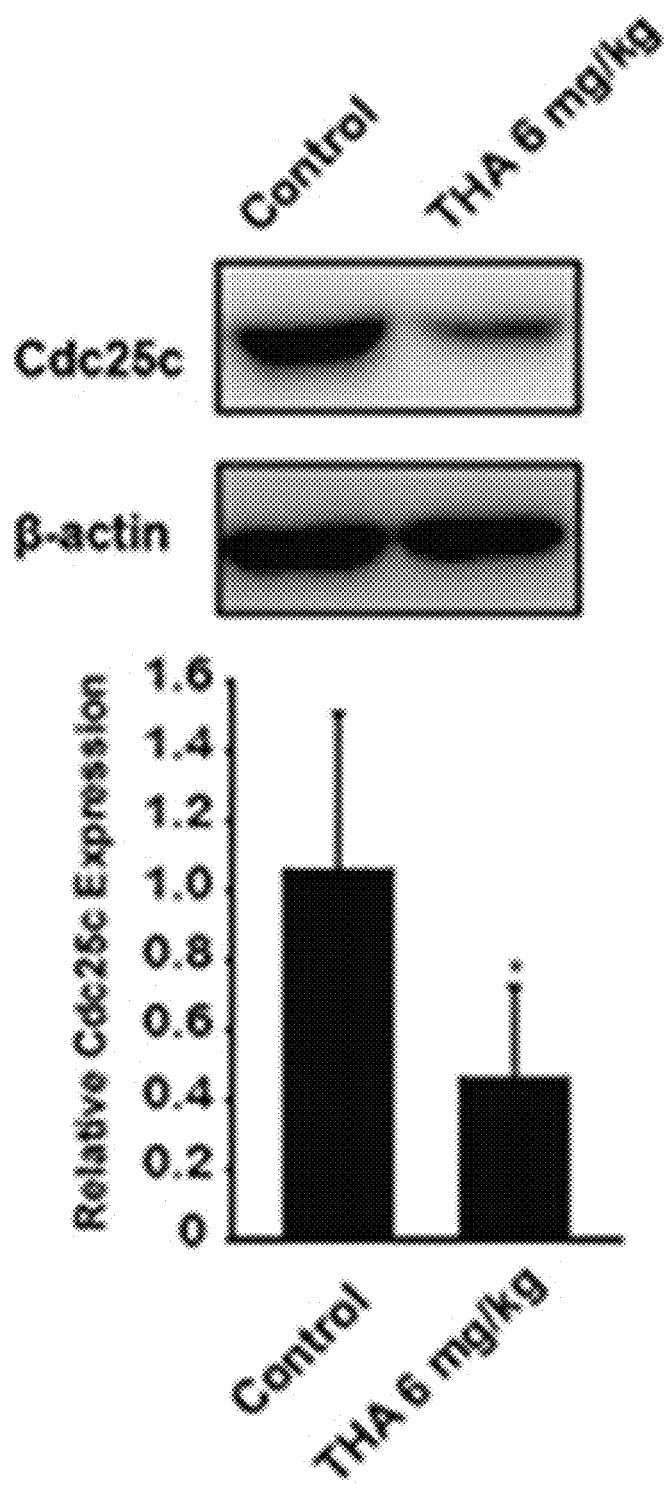

As a result, it was confirmed as illustrated in FIGS. 7A to 7F that tumor size (see FIG. 7A) and tumor weight (see FIG. 7C) were significantly reduced upon treatment with THA, as compared to a control, the body weight of each mouse was observed to be maintained at a similar level (see FIG. 7B), PCNA, which is an actual cell proliferative index, was reduced in a group treated with 6 mg/kg of THA, and TUNEL, which is an apoptotic index, was significantly increased (see FIGS. 7D and 7E). It was also confirmed that cdc25c expression was significantly inhibited in a group treated with THA (see FIG. 7F).

In addition, THA was administered to a tamoxifen-resistant breast cancer cell-transplanted mouse model at a dose of 10 mg/kg, 30 mg/kg, or 100 mg/kg using an oral zonde needle every day for 2 weeks.

Figure 7G:
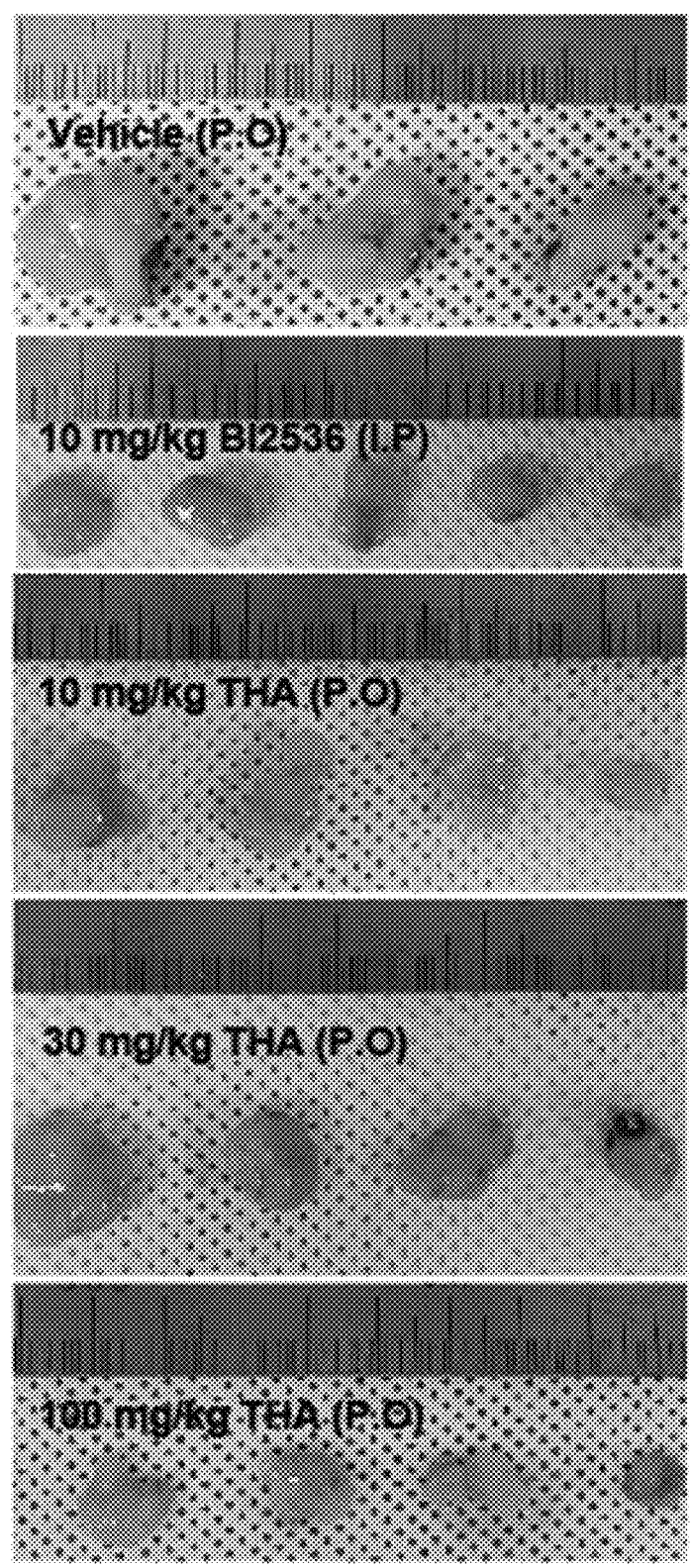
FIGS. 7G to 7I illustrate results of confirming an anticancer effect upon oral administration of THA.
Figure 7H:
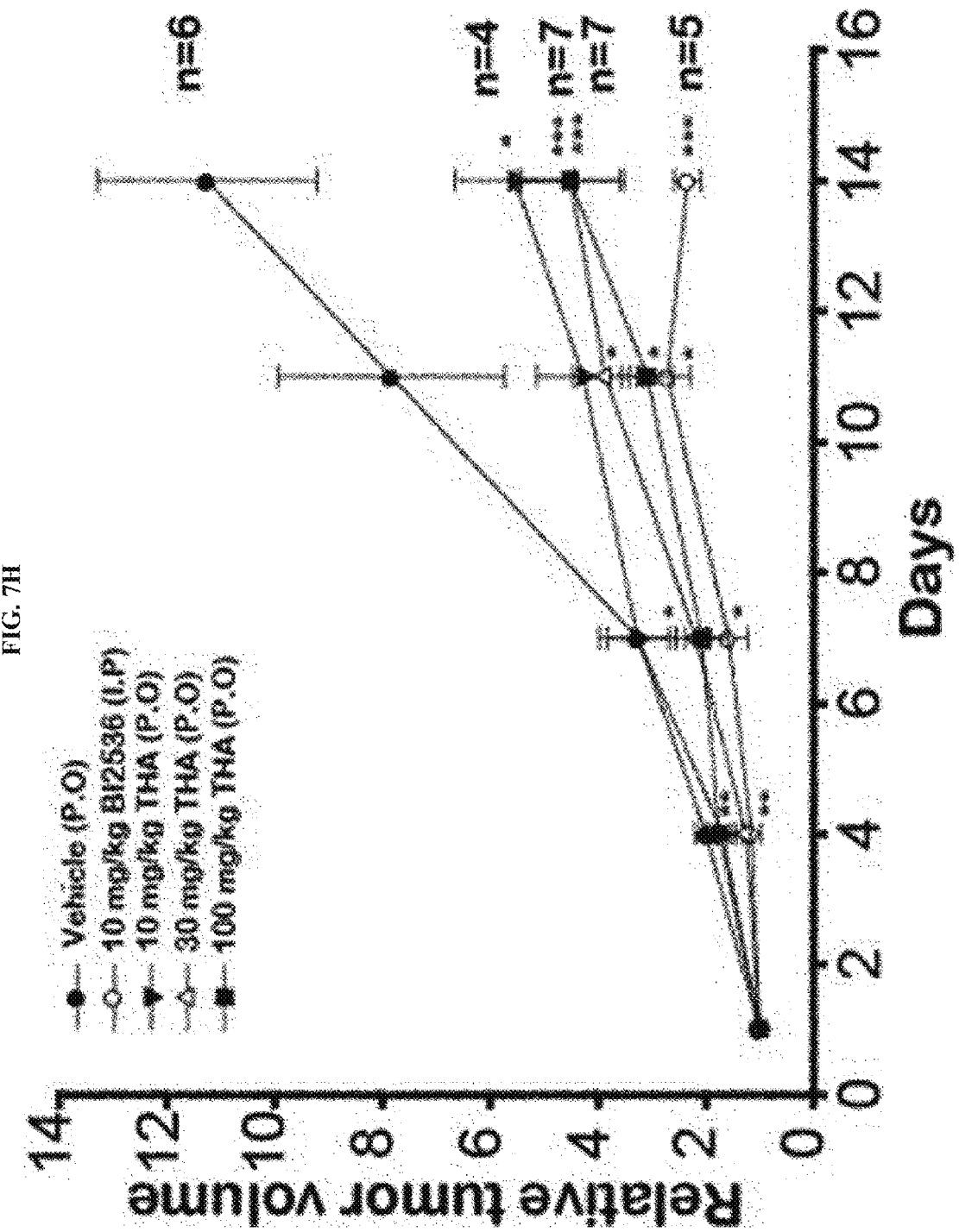
Figure 7I:
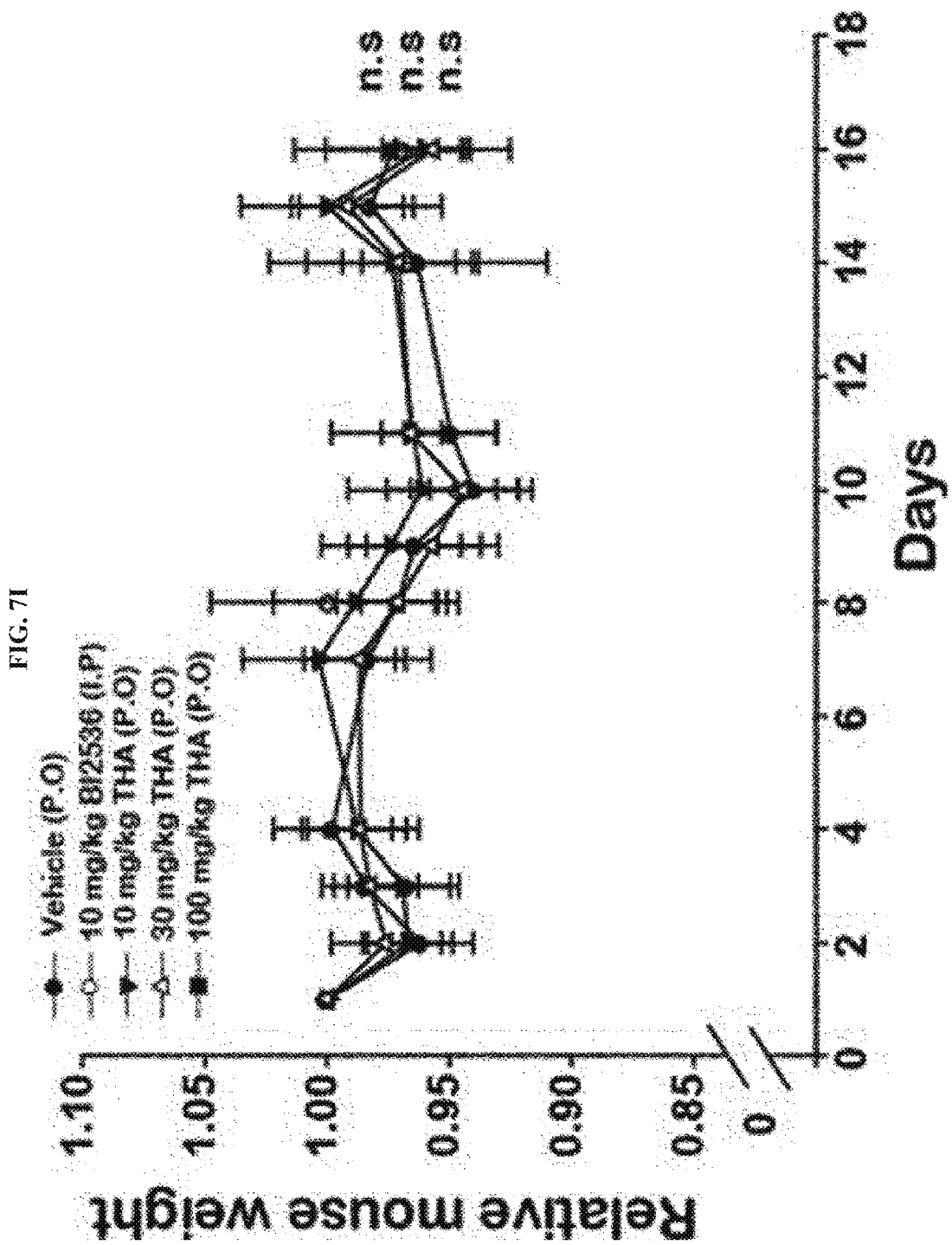

As a result, it was confirmed as illustrated in FIGS. 7G to 7I that, when THA was orally administered at a dose of 10 mg/kg, 30 mg/kg, or 100 mg/kg, the tumor size was significantly reduced compared to that of a control (see FIG. 7G), this is illustrated in FIG. 7H, and it was observed that the body weight of each mouse was maintained at a similar level even when THA was administered (see FIG. 7I). As such, THA exhibits an excellent anticancer activity when orally administered, and thus it can be seen that THA is an effective oral drug.

From the above-described results, it was confirmed that *Curcuma comosa*, particularly THA inhibited tumor proliferation in a tamoxifen-resistant breast cancer xenograft model, from which it was confirmed that it was able to prevent or treat breast cancer or hormone-resistant breast cancer.

Example 4. Confirmation of Plk1 Expression Patterns in Tissues and Cells of Human Breast Cancer Patients 4-1. Plk1 Expression Distribution in Tissues of Human Breast Cancer Patients To confirm the expression/distribution of polo-like kinase 1 (Plk1) in tissues of human breast cancer patients, each tissue fixed in 10% formalin was embedded in paraffin using a general method, and then 4 μm sections were prepared using a microtome and attached to slides, followed by removal of the paraffin with xylene and rinsing. As an antigen recovery process, the slides were heated in Tris-EDTA buffer (pH 8.0) in a constant-temperature water bath for 40 minutes. After washing the slides with distilled water, the sections were treated with a peroxidase blocking buffer at room temperature for 10 minutes to remove endogenous peroxidase, an anti-Plk1 antibody was diluted 1:50, 300 μl of the diluted antibody was added thereto to allow a reaction to occur at 4° C. overnight.

Subsequently, the slides were washed with TBS buffer (TBST) supplemented with 0.1% Tween 20, and then allowed to react with 300 μl of a rabbit enhancer in a POLPOL 2 Plus kit manufactured by GBI at room temperature for 30 minutes, followed by washing again with TBST, and 300 μl of a polymer-HRP solution was added thereto to allow a reaction to occur at room temperature for 30 minutes. The slides were washed again with TBST and color development was carried out with diaminobenzidine (DAB). At this time, the color development time was 5 minutes, and after washing, the sections were allowed to react with Mayer's hematoxylin for 1 minute, and then immersed in TBST to perform a bluing process. The washed slides were dehydrated with alcohol and xylene and then sealed with MM-24.

Figure 8:
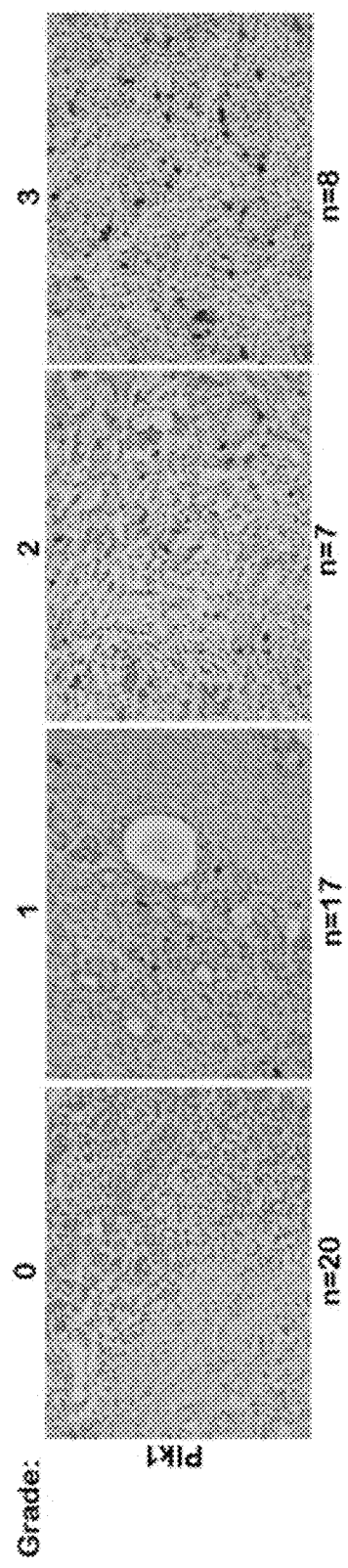
FIG. 8 illustrates results of confirming Plk1 expression/distribution patterns in tissues of human breast cancer patients.

As a result, it was confirmed as illustrated in FIG. 8 that Plk1 expression/distribution patterns were exhibited in tissues of human breast cancer patients in which 61% of the tissues were positive.

4-2. Comparison Between Plk1 Expression Levels in Human Breast Cancer Cell Line Panel To compare expression levels of Polo-like kinase 1 (Plk1) in a human breast cancer cell line panel, sodium dodecyl sulfate-polyacrylamide gel electrophoresis (SDS-PAGE) was performed using a gel electrophoresis apparatus (Mighty Small SE250, Hoefer Scientific Instruments, San Francisco). A cell lysate fraction was diluted in a sample dilution buffer [63 mM Tris (pH 6.8), 10% glycerol, 2% SDS, 0.0013% bromophenol blue, and 5% β-mercaptoethanol], and then electrophoresis was performed thereon in an electrode buffer (15 g of Tris, 72 g of glycerin, and 5 g of SDS included in a 1 L solution) using a 8% to 12% gel. The electrophoresed gel was used to transfer proteins to a nitrocellulose membrane at 190 mAmps for 70 minutes in a transfer buffer (25 mM Tris, 192 mM glycerin, and 20% v/v methanol (pH 8.3)) using a transfer electrophoresis apparatus.

Subsequently, the nitrocellulose membrane was reacted with a primary antibody, and then reacted with horseradish peroxidase-conjugated goat anti-rabbit IgG and horseradish peroxidase-conjugated goat anti-mouse IgG as secondary antibodies for 6 hours, followed by color development using an ECL detection system (ECL chemiluminescence system, Amersham, Gaithersberg, Mass.).

Figure 9:
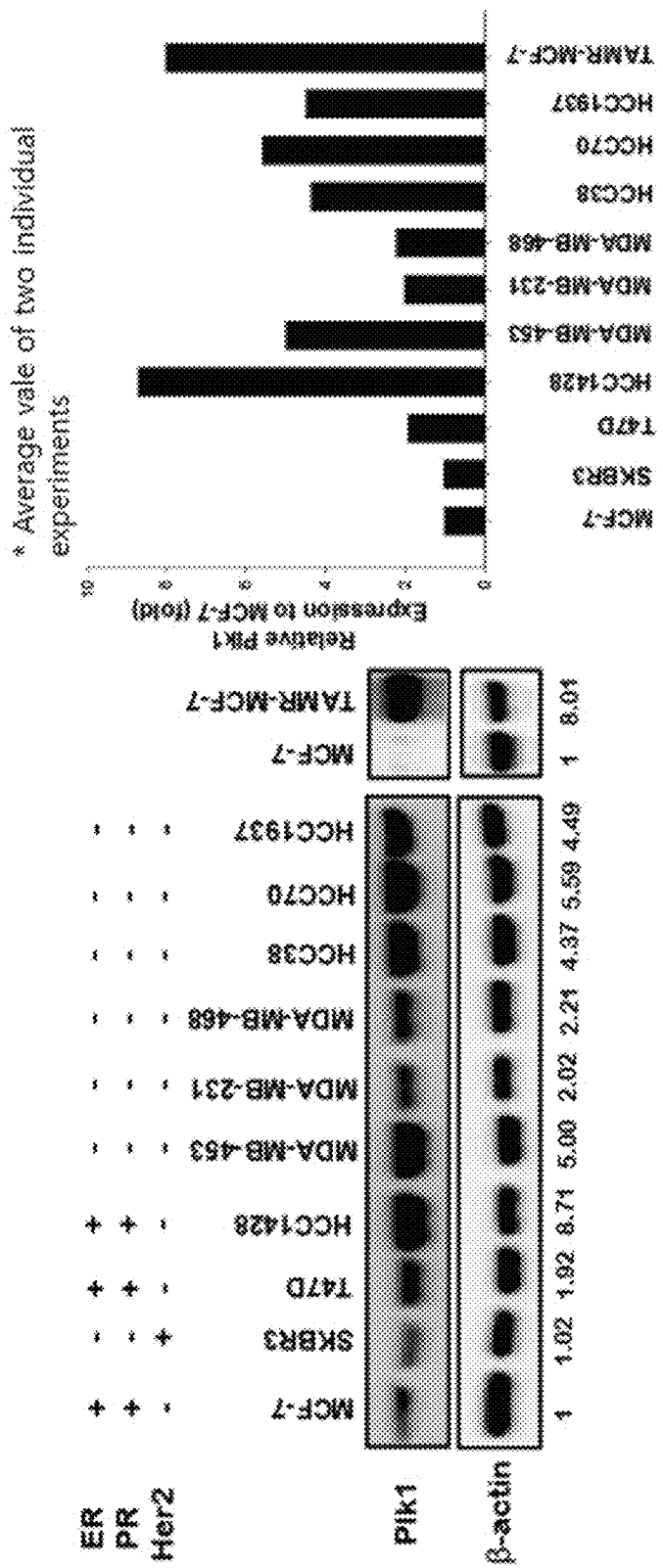
FIG. 9 illustrates results of confirming the expression of Plk1 in a human breast cancer cell line panel by western blotting and immunofluorescence imaging.

As a result of examining Plk1 expression in MCF-7, SKBR3, T47D, HCC1428, MDA-MB-453, MDA-MB-231, MDA-MB-468, HCC38, HCC70, HCC1937, and TAMR-MCF-7 breast cells by western blotting and immunofluorescence imaging, it was confirmed as illustrated in FIG. 9 that the Plk1 expression was increased in the SKBR3, T47D, HCC1428, MDA-MB-453, MDA-MB-231, MDA-MB-468, HCC38, HCC70, HCC1937, and TAMR-MCF-7 breast cancer cells, as compared to that in MCF-7. The right graph of FIG. 9 shows an average value of results of two repeated experiments.

Example 5. Confirmation of THA Reactivity Per Each Human Breast Cancer Cell Line 5-1. Measurement of Cell Proliferation Inhibitory Activity of BI-2536 and THA Per Human Breast Cancer Cell Line To measure cell proliferation, SKBR3, T47D, HCC1428, MDA-MD-453, MDA-MB-231, MDA-MB-468, HCC38, HCC70, and HCC1937 cells were plated in respective 96-well dishes ($5 \times 10^3$ cells/well). For cell stabilization, these cells were incubated in a cell incubator at 36.5° C. for 24 hours, and then treated with a drug, and the number of live cells was measured using an IncuCyte ZOOM live cell analysis system (Essen Bioscience, Ann Arbor, Mich., USA) at intervals of 4 hours.

Figure 10A:
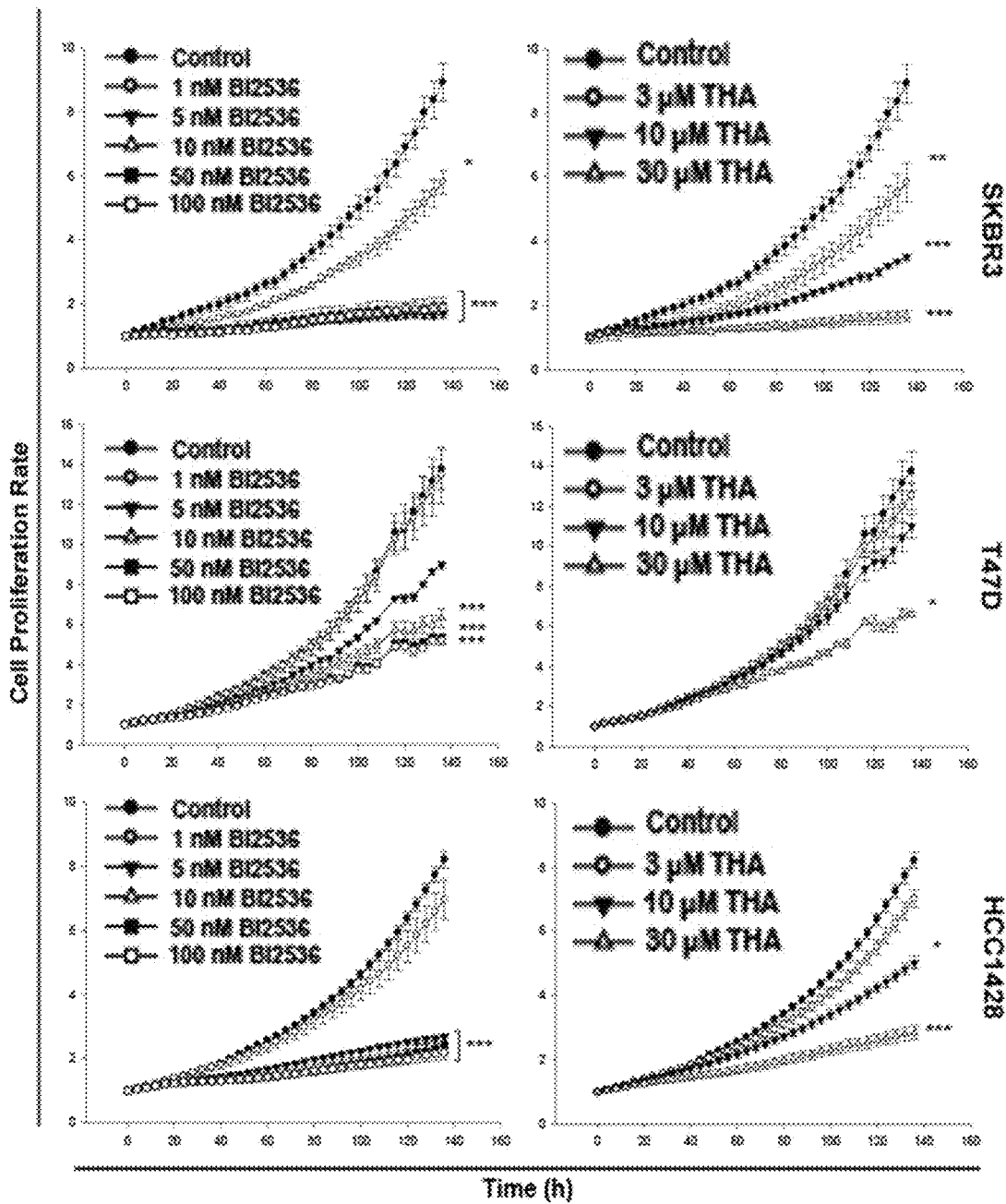
FIGS. 10A to 10C illustrate results of confirming cell proliferation inhibitory activities according to treatment with BI-2536 and THA per human breast cancer cell line.
Figure 10B:
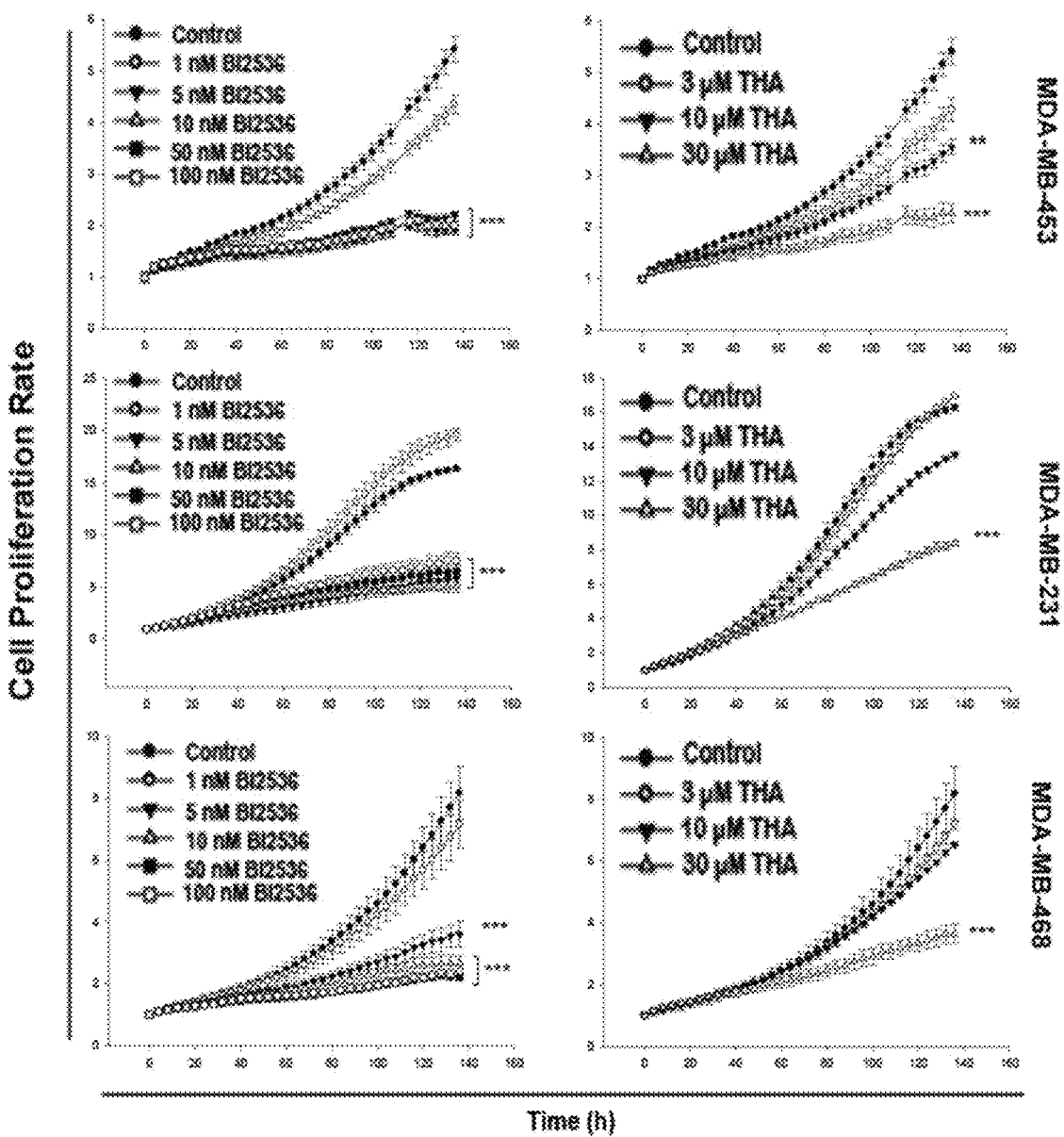
Figure 10C:
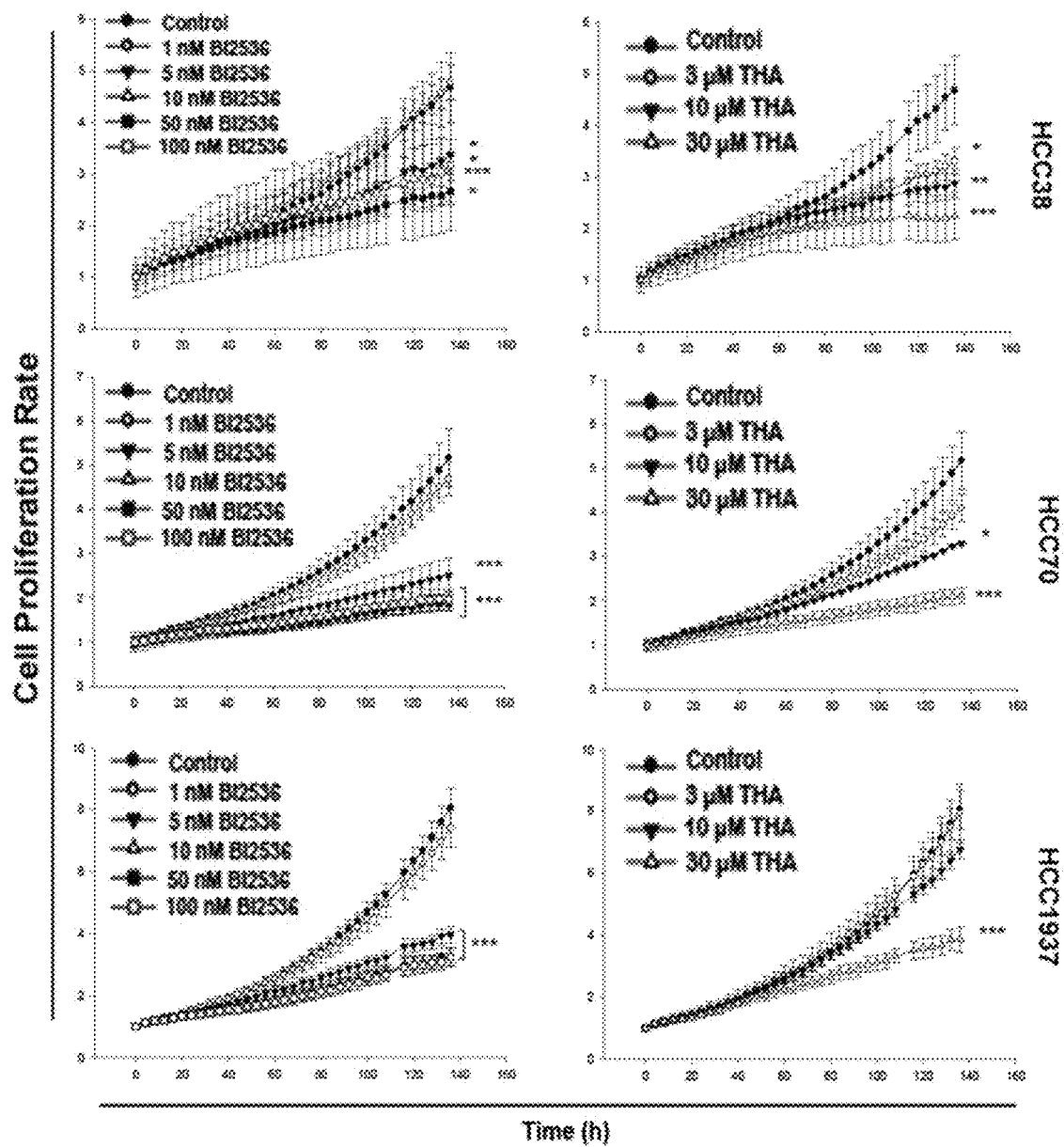

As a result, it was confirmed as illustrated in FIGS. 10A to 10C that, as the treatment amounts of BI-2536 and THA for SKBR3, T47D, and HCC1428 cells (see FIG. 10A), MDA-MD-453, MDA-MB-231, and MDA-MB-468 cells (see FIG. 10B), and HCC38, HCC70, and HCC1937 cells (see FIG. 10C) increased, cell proliferation was inhibited.

Figure 11B:
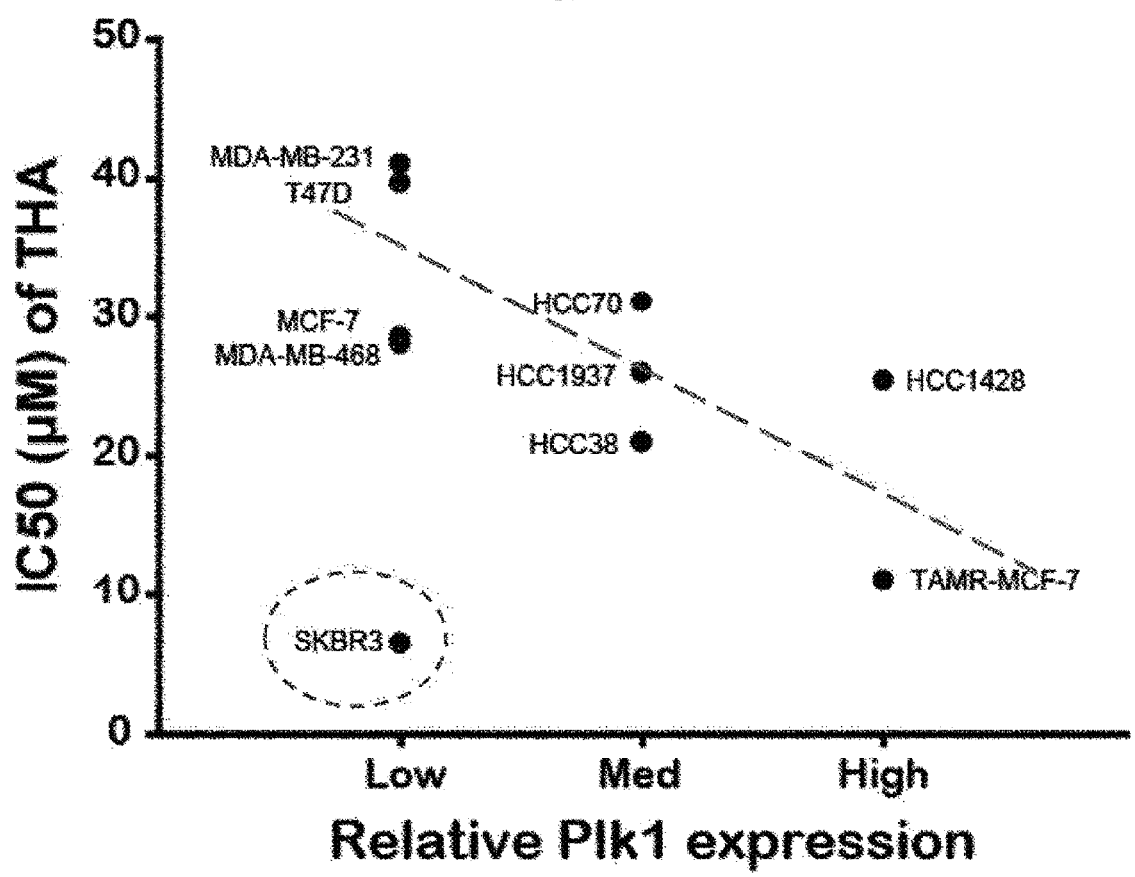

5-2. Changes in THA Reactivity According to Plk1 Expression Differences Per Human Breast Cancer Cell Line To analyze changes in THA reactivity according to Plk1 expression differences per human breast cancer cell line, the expression levels of Plk1 of the SKBR3, T47D, HCC1428, MDA-MB-453, MDA-MB-231, MDA-MB-468, HCC38, HCC70, HCC1937, and TAMR-MCF-7 cells compared to that of MCF-7, which were confirmed in Example 4-2, were classified as low (1 to 3), medium (3 to 6), and high (6 to 9), and as illustrated in FIG. 11A, IC50 values of the MCF-7, SKBR3, T47D, HCC1428, MDA-MB-453, MDA-MB-231, MDA-MB-468, HCC38, HCC70, HCC1937, and TAMR-MCF-7 cells were obtained based on the cell proliferation inhibition graph confirmed in Example 5-1. In addition, as illustrated in FIG. 11B, the correlation between Plk1 expression and IC50 of each cell line was represented as a graph.

From the above results, it can be seen that THA selectively acts on breast cancer cells with high Plk1 expression, and thus it is anticipated that THA can be effectively used for the treatment of Plk1-positive breast cancer.

The above description of the present invention is provided for illustrative purposes only, and it will be understood by one of ordinary skill in the art to which the present invention pertains that the invention may be embodied in various modified forms without departing from the spirit or essential characteristics thereof. Thus, the embodiments described herein should be considered in an illustrative sense only and not for the purpose of limitation.

INDUSTRIAL APPLICABILITY

The present invention relates to a composition for preventing, alleviating, or treating breast cancer, which comprises 2,4,6-trihydroxyacetophenone (THA) as an active ingredient, and it is anticipated that, when treated, the composition can be effective for preventing, alleviating, or treating tamoxifen-resistant breast cancer or polo-like kinase 1 (Plk1)-overexpressing breast cancer.

The invention claimed is:

1. A method of treating breast cancer, the method comprising administering a pharmaceutical composition comprising 2,4,6-trihydroxyacetophenone (THA) as an active ingredient to an individual in need thereof, wherein the breast cancer is tamoxifen-resistant breast cancer.

2. The method of claim 1, wherein the pharmaceutical composition inhibits the activity of polo-like kinase 1 (Plk1).

3. A method of alleviating breast cancer, the method comprising administering a health functional food composition comprising 2,4,6-trihydroxyacetophenone(THA) as an active ingredient to an individual in need thereof, wherein the breast cancer is tamoxifen-resistant breast cancer.

4. The method of claim 3, wherein the health functional food composition inhibits the activity of polo-like kinase 1 (Plk1).

\* \* \* \* \*